US012691214B2

(12) United States Patent
Taniguchi et al.

(10) Patent No.: US 12,691,214 B2
(45) Date of Patent: Jul. 28, 2026

(54) SYRINGE HOLDER AND PACKAGE

(71) Applicant: TAISEI KAKO CO., LTD., Osaka (JP)

(72) Inventors: Kensuke Taniguchi, Osaka (JP); Tomoyuki Sonoyama, Osaka (JP); Yuki Katagiri, Osaka (JP); Miku Hori, Osaka (JP); Ippei Matsumoto, Osaka (JP)

(73) Assignee: TAISEI KAKO CO., LTD., Osaka (JP)

( * ) Notice: Subject to any disclaimer, the term of this patent is extended or adjusted under 35 U.S.C. 154(b) by 0 days.

(21) Appl. No.: 18/877,181

(22) PCT Filed: Jul. 5, 2023

(86) PCT No.: PCT/JP2023/024859
§ 371 (c)(1),
(2) Date: Dec. 19, 2024

(87) PCT Pub. No.: WO2024/010018
PCT Pub. Date: Jan. 11, 2024

(65) Prior Publication Data
US 2025/0375567 A1     Dec. 11, 2025

(30) Foreign Application Priority Data
Jul. 8, 2022     (JP) ................................. 2022-110458

(51) Int. Cl.
*A61M 5/00*          (2006.01)
*B65D 25/10*         (2006.01)

(52) U.S. Cl.
CPC ............ *A61M 5/002* (2013.01); *A61M 5/001* (2013.01); *B65D 25/108* (2013.01)

(58) Field of Classification Search
CPC ...... A61B 50/30; A61B 50/33; B65D 25/108; B65D 25/34; B65D 1/36; B65D 81/203;
(Continued)

(56) References Cited

U.S. PATENT DOCUMENTS

| | | |
|---|---|---|
| 5,372,252 A | 12/1994 | Alexander |
| 10,227,161 B2 | 3/2019 | Auerbach |

(Continued)

FOREIGN PATENT DOCUMENTS

| | | |
|---|---|---|
| JP | 2006-513782 A | 4/2006 |
| JP | 2013-521842 A | 6/2013 |

(Continued)

OTHER PUBLICATIONS

International Search Report for the International application No. PCT/JP2023/024859 mailed on Sep. 5, 2023, with English translation provided by WIPO.

(Continued)

*Primary Examiner* — King M Chu
(74) *Attorney, Agent, or Firm* — Ladas & Parry, LLP

(57)          ABSTRACT

A syringe holder includes a base plate portion, and a tube portion which is formed in a tubular shape having an axis direction being provided along a plate thickness direction of the base plate portion and through which a syringe is capable of being inserted from one side to another side in the axis direction. The syringe includes a tubular syringe body and a flange portion which protrudes from the syringe body to a radially outer side. The tube portion includes a flange support portion which supports the flange portion of the inserted syringe from the other side in the axis direction and a flange abutting portion which is arranged on the one side in the axis direction and on a radially outer side, relative to the flange support portion, and which is capable of abutting, in the radial direction, the flange portion supported by the flange support portion.

3 Claims, 15 Drawing Sheets

(58) Field of Classification Search
CPC ....... B65D 71/70; A61M 5/002; A61M 5/008;
A61M 5/001; A61M 5/3202; A61M
5/3135; A61M 2005/3104; A61M 5/3134;
A61M 5/344; A61M 2005/312; A61M
5/34
USPC ..... 206/366, 364, 365, 524.8, 370; 604/192;
211/60.1
See application file for complete search history.

(56) References Cited

U.S. PATENT DOCUMENTS

| | | |
|---|---|---|
| 2007/0151882 A1 | 7/2007 | Cocheteux et al. |
| 2012/0234710 A1 | 9/2012 | Finke |
| 2013/0001117 A1* | 1/2013 | Liversidge ............. A61B 50/33 |
| | | 206/370 |
| 2015/0190566 A1* | 7/2015 | Okihara .............. A61M 5/3134 |
| | | 206/365 |
| 2020/0390967 A1 | 12/2020 | Mason et al. |

FOREIGN PATENT DOCUMENTS

| | | | | |
|---|---|---|---|---|
| JP | 2021-515729 A | 6/2021 | | |
| WO | 2013/031266 A | 3/2013 | | |
| WO | 2014049712 A1 | 4/2014 | | |
| WO | 2014049713 A1 | 4/2014 | | |
| WO | 2014102987 A1 | 7/2014 | | |
| WO | WO-2019171192 A1 * | 9/2019 | ............ | A61M 5/008 |

OTHER PUBLICATIONS

Written Opinion of the International Searching Authority for International application No. PCT/JP2023/024859 mailed on Sep. 5, 2023, with English translation provided by WIPO.
International Preliminary Report on Patentability for the International application No. PCT/JP2023/024859 issued on Dec. 18, 2024 and its English translation provided by WIPO.
Extended search report from corresponding European Patent Application No. 23835549.9 dated Mar. 30, 2026.

* cited by examiner

SYRINGE HOLDER AND PACKAGE

CROSS-REFERENCE TO RELATED APPLICATIONS

This application is the national stage of International Application No. PCT/JP2023/024859 filed on Jul. 5, 2023, which claims priority to Japanese Patent Application No. 2022-110458 filed on Jul. 8, 2022, the disclosures of which are incorporated herein by reference in their entireties.

FIELD

The present disclosure relates to a syringe holder which holds a syringe and a package which includes the syringe holder.

BACKGROUND

As the syringe holder, for example, a nest plate disclosed in Patent Literature 1 has been present. An outer diameter of this nest plate is a generally rectangular shape. The nest plate has a plurality of receiving tubes. The receiving tube is a hollow cylinder which passes through the nest plate.

By using the nest plate, an injection tube as the syringe, in which a flange is provided in an outer periphery portion of a proximal end opening portion, is inserted in and suspended from the receiving tube. Specifically, the injection tube is, from its distal end, inserted in the receiving tube to be capable of being inserted and extracted and is locked in and suspended from the receiving tube by the flange. Further, the nest plate is placed on a shelf of a plastic container body whose upper surface is open, and an injection tube housing container is thereby assembled. Furthermore, the injection tube housing container, which has been subjected to a sterilization treatment in a state where an internal portion is tightly sealed, is transported to a factory where filling with an agent is performed.

CITATION LIST

Patent Literature

Patent Literature 1: International Publication No. WO 2014/049712

Incidentally, for example, in order to accurately fill the injection tube, which is inserted in the receiving tube, with the agent, it has been demanded that positioning of the injection tube with respect to the receiving tube be performed highly precisely. However, in the above Patent Literature 1, an inner diameter of the receiving tube is larger than an outer diameter of a barrel portion of the injection tube. Thus, when the injection tube is transported in a state where the injection tube is inserted in the receiving tube and locked and suspended by the flange, the injection tube moves in the receiving tube due to vibration or the like in transportation. Thus, there is a problem that the injection tube is displaced with respect to the receiving tube.

SUMMARY

Technical Problem

Accordingly, an object of the present disclosure is to provide a syringe holder that can highly precisely perform positioning of a syringe with respect to a tube portion and a package that includes the syringe holder.

Solution to Problem

The present disclosure provides a syringe holder including: a base plate portion having a plate shape; and a tube portion being formed in a tubular shape having an axis direction being provided along a plate thickness direction of the base plate portion, the tube portion being configured to allow a syringe to be inserted through the tube portion from one side to another side in the axis direction, the syringe including a syringe body which has a tubular shape and a flange portion which protrudes from an outer periphery surface of the syringe body to an outer side in a radial direction, in which the tube portion includes a flange support portion which supports the flange portion of the inserted syringe from the other side in the axis direction and a flange abutting portion which is arranged on the one side in the axis direction and on an outer side in the radial direction, relative to the flange support portion, the flange abutting portion being configured to be capable of abutting, in the radial direction, the flange portion supported by the flange support portion.

Further, the syringe holder can be configured such that the tube portion includes a syringe abutting portion, and the syringe abutting portion is arranged on the other side in the axis direction and on an inner side in the radial direction, relative to the flange support portion, and is configured to be capable of abutting a portion of the syringe body, the portion being in vicinity to the flange portion in the syringe body on the other side in the axis direction relative to the flange portion.

Further, the syringe holder can be configured such that the syringe body includes a trunk portion which has a tubular shape and stores a solution, the syringe includes a large-diameter portion arranged in a distal end portion of the trunk portion and configured to be larger than the trunk portion in the radial direction, the tube portion includes a large-diameter guide portion which guides the large-diameter portion to an inner side in the radial direction, and the large-diameter guide portion is arranged on the other side in the axis direction relative to the syringe abutting portion and is configured to have a diameter decreasing from the other side toward the one side in the axis direction.

Further, the syringe holder can be configured such that the tube portion includes a flange guide portion which guides the flange portion to an inner side in the radial direction, and the flange guide portion is arranged on the one side in the axis direction and on an outer side in the radial direction, relative to the flange abutting portion, and is configured to have a diameter decreasing from the one side toward the other side in the axis direction.

Further, the present disclosure provides a package including: the syringe holder which is described above; the syringe; and a container body for housing the syringe holder.

BRIEF DESCRIPTION OF DRAWINGS

FIG. 9 is a perspective view of a syringe holder according to a different form from the above embodiment.

FIG. 13 is a vertical cross-sectional view of the syringe holder in a different form.

DESCRIPTION OF EMBODIMENTS

One embodiment of the present disclosure will hereinafter be described based on FIGS. 1 to 8.

Figure 1:
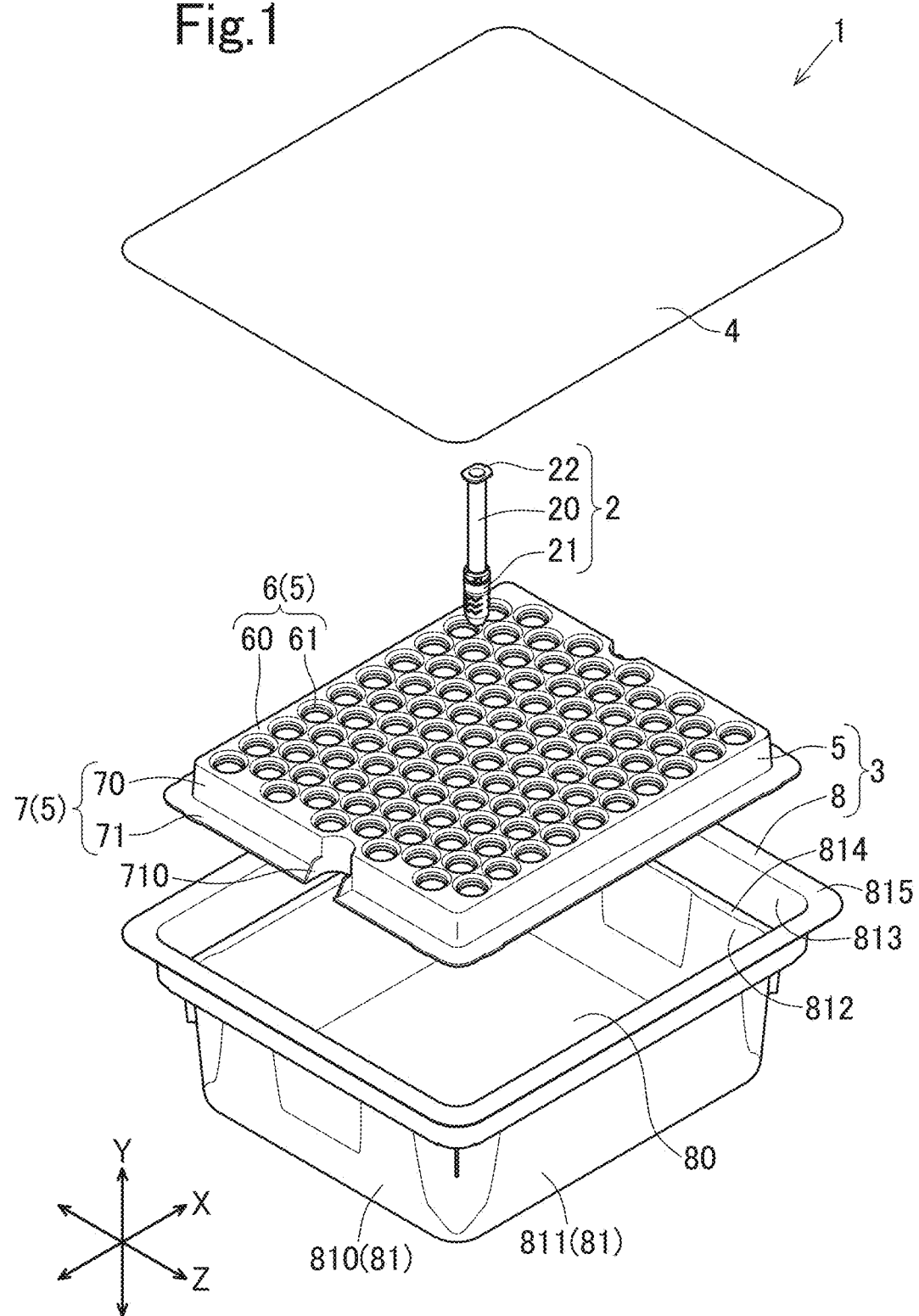
FIG. 1 is a perspective view of a package according to one embodiment of the present disclosure.

In the following description, a direction in which a syringe 2 is inserted in and pulled from a syringe holder 5 will be specified as an "axis direction Y". Further, a direction orthogonal to the axis direction Y will be specified as a "radial direction". In addition, a direction around the axis direction Y will be specified as a "circumferential direction". Further, as shown in FIG. 1, the radial direction includes a lateral direction X and a vertical direction Z which are orthogonal to each other. In addition, in the axis direction Y, an upper side in FIG. 1 will be set as one side, and a lower side in FIG. 1 will be set as the other side.

FIG. 1 shows a package 1. The package 1 is used when being transported in a state where the syringe 2 is held. The package 1 includes the syringe 2, a syringe housing container 3, and a protection film 4. Here, the package 1 is transported in an inverted posture which will be described later. Thus, it is necessary to cause the syringe 2 not to fall from the package 1 when the package 1 is set to the inverted posture. Accordingly, the package 1 includes at least the protection film 4. Further, when the package 1 of the present embodiment is assembled, a protection cover (not shown) and a sterilization bag (not shown) are used which will be described later. Accordingly, the package 1 of the present embodiment includes the protection cover and the sterilization bag.

Figure 5:
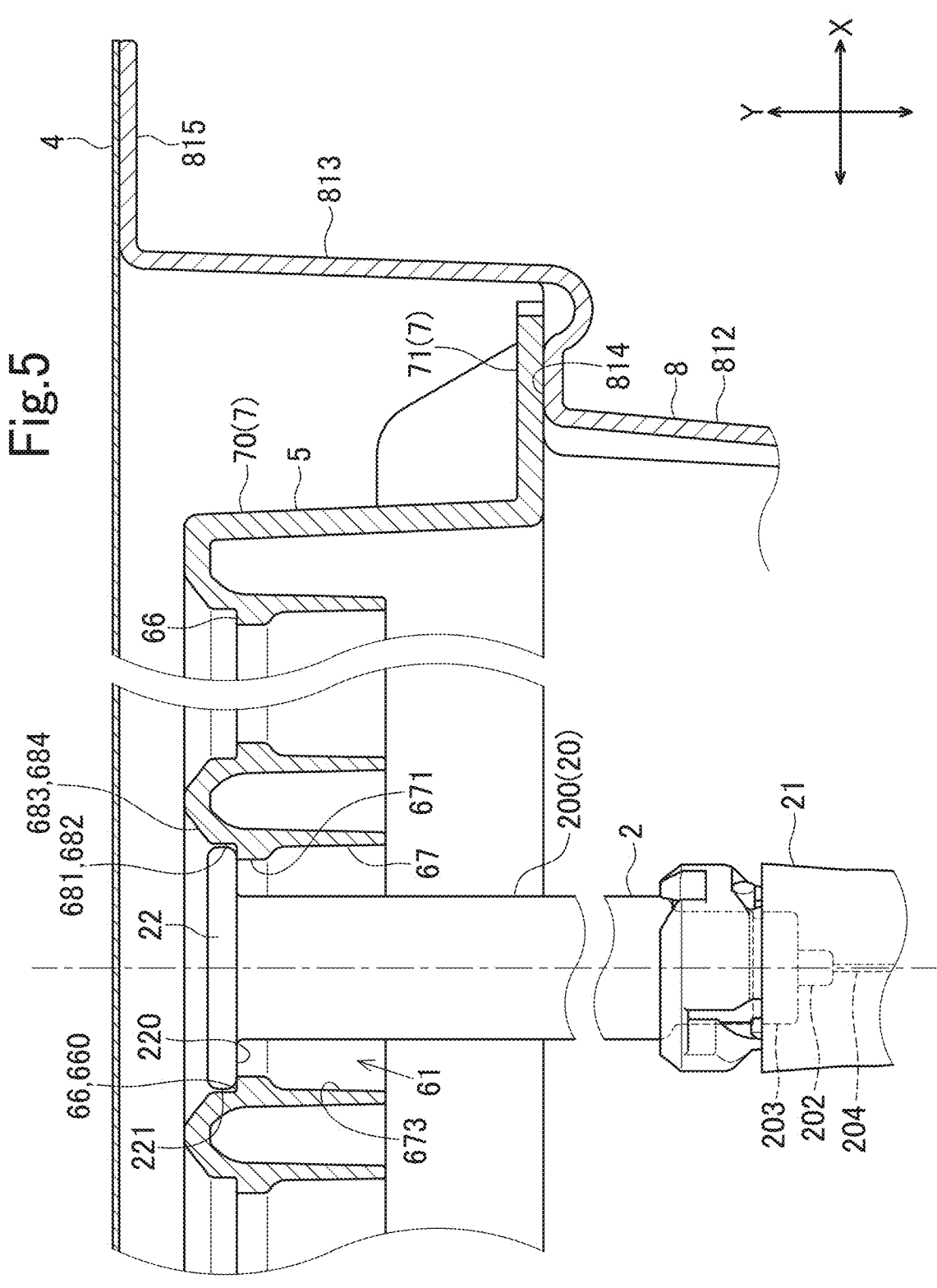
FIG. 5 is an enlarged cross-sectional view of the package according to the embodiment.

The syringe 2 is used for injection and suction of a solution. As shown in FIGS. 1 and 5, the syringe 2 includes a syringe body 20 having a tubular shape, a cap 21 which covers a distal end portion of the syringe body 20, and a flange portion 22 which is provided in an outer periphery surface of the syringe body 20. Further, the syringe 2 of the present embodiment includes an injection needle 204 which is fixed to a distal end of the syringe body 20.

The syringe body 20 is provided for storing and discharging a solution. The syringe body 20 has rigidity. The syringe body 20 is made of glass or a hard resin (for example, plastic), through which an inside can be viewed, for example. As shown in FIG. 5, the syringe body 20 includes a trunk portion 200 which stores a solution, a holding portion 202 which holds the injection needle 204 for discharging a solution, and a periphery tube portion 203 which is formed in a periphery of the holding portion 202.

The trunk portion 200 has a tubular shape. Thus, the trunk portion 200 includes one end and the other end in the axis direction Y in addition to an inner periphery surface and an outer periphery surface. The trunk portion 200 of the present embodiment has a cylindrical shape. Further, the trunk portion 200 of the present embodiment has a constant length in the radial direction in each position in the axis direction Y. Thus, in the trunk portion 200 of the present embodiment, the inner periphery surface and the outer periphery surface extend in the axis direction Y. The one end (hereinafter referred to as a proximal end) of the trunk portion 200 in the axis direction Y is open. The other end (hereinafter referred to as a distal end) of the trunk portion 200 in the axis direction Y is closed except a portion for inserting the injection needle 204. Thus, the trunk portion 200 can be filled with a solution from the one side in the axis direction Y. The trunk portion 200 of the present embodiment has a drug solution filling portion (not numbered) as a portion to be filled with a drug solution as the solution. Specifically, the drug solution filling portion denotes a portion, in the trunk portion 200, from a solution surface to a distal end of the filled drug solution. Note that the trunk portion 200 is filled with the drug solution such that a length of the drug solution filling portion in the axis direction Y becomes shorter than a separation distance between the distal end of the trunk portion 200 and the flange portion 22 which will be described later.

The holding portion 202 is provided at the distal end of the trunk portion 200. The holding portion 202 is configured to have a tubular shape which extends in the axis direction Y. An inside of the tubular holding portion 202 communicates with the portion for inserting the injection needle 204 at the distal end of the trunk portion 200, and the holding portion 202 thereby communicates with an inside of the tubular trunk portion 200. Note that the holding portion 202 is shorter in the axis direction Y and has a diameter smaller than the trunk portion 200.

The periphery tube portion 203 is formed into a cylindrical shape. An inner diameter of the periphery tube portion 203 is larger than an outer diameter of the holding portion 202. As shown in FIG. 5, the periphery tube portion 203 is provided at the distal end of the trunk portion 200 so as to surround the holding portion 202 in the radial direction. An outer diameter of the periphery tube portion 203 of the present embodiment is smaller than an outer diameter of the trunk portion 200. Note that the periphery tube portion 203 is shorter than the holding portion 202 in the axis direction Y.

Figure 7:
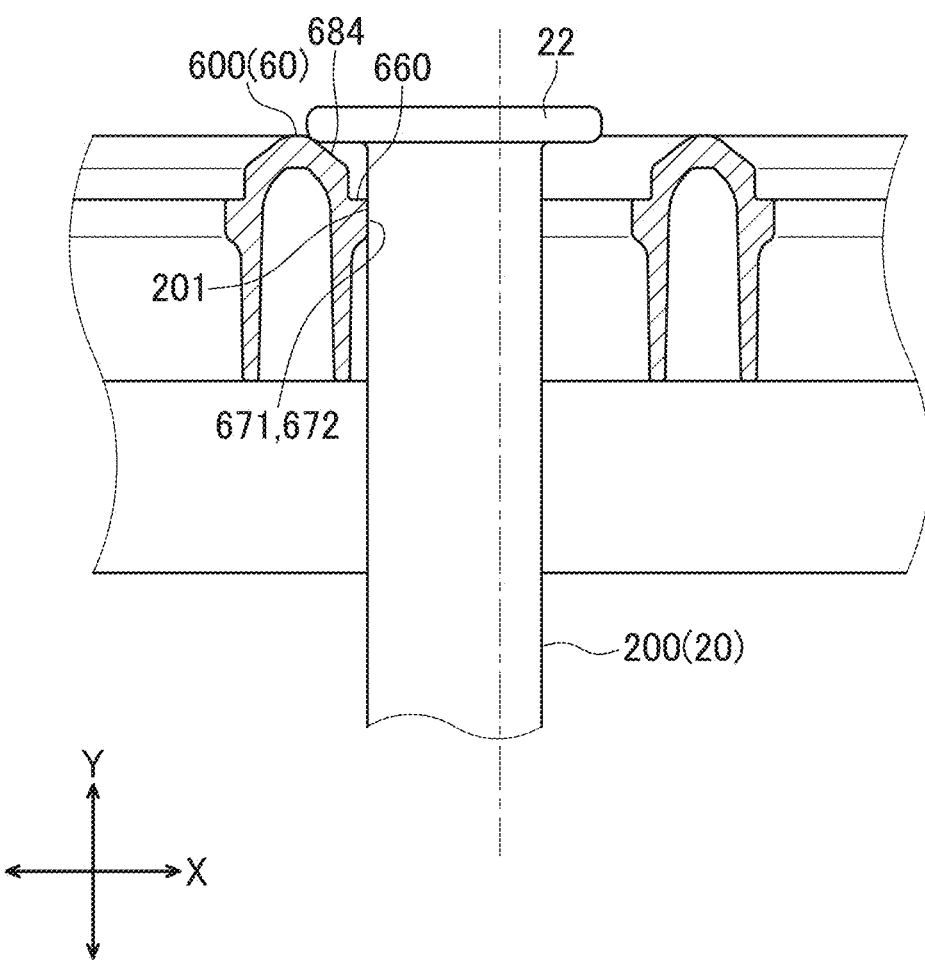
FIG. 7 is an enlarged cross-sectional view of the syringe holder according to the embodiment and is a diagram showing a state where a trunk portion abuts a syringe abutting portion.

As shown in FIG. 7, the syringe body 20 has an abutting portion 201. The abutting portion 201 is a portion on the other side in the axis direction Y of the flange portion 22 which will be described later. Specifically, the abutting portion 201 is a portion, in which the syringe 2 inserted through a tube portion 61 abuts a syringe abutting portion 671 when the syringe 2 moves in the tube portion 61, in the portion on the other side in the axis direction Y of the flange portion 22. The abutting portion 201 is a vicinity portion of the flange portion 22 in the outer periphery surface of the trunk portion 200. Specifically, the abutting portion 201 is a region between the drug solution filling portion of the trunk portion 200 and the flange portion 22. Thus, the abutting portion 201 is arranged on the one side in the axis direction Y of the drug solution filling portion. Note that the abutting portion 201 is formed in a whole circumference of the outer periphery surface of the trunk portion 200.

The injection needle 204 is inserted in the holding portion 202. Thus, the solution reserved in the syringe body 20 is discharged from the syringe body 20 via the injection needle 204 inserted in the holding portion 202 which communicates with the distal end of the trunk portion 200.

Figure 8:
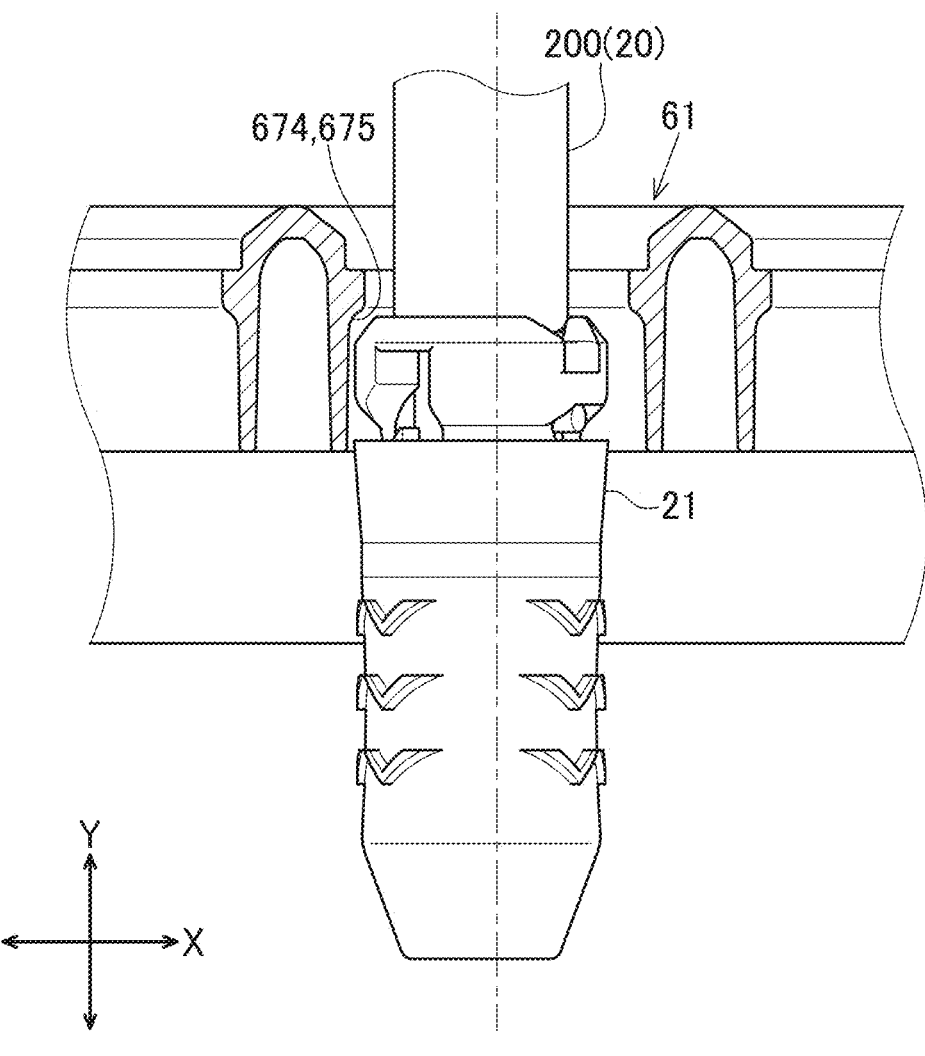
FIG. 8 is an enlarged cross-sectional view of the syringe holder according to the embodiment and is a diagram showing a state where a cap is pulled from a tube portion.

As shown in FIGS. 1 and 5, the cap 21 is configured to have a bottomed tubular shape in which a distal end portion on the other side in the axis direction Y is closed. The cap 21 of the present embodiment is attached to the periphery tube portion 203 in a state where the cap 21 covers the injection needle 204 from the axis direction Y and the circumferential direction and thereby covers the distal end portion of the syringe body 20. Thus, as shown in FIG. 1, the cap 21 is arranged on the distal end side of the syringe body 20 in the axis direction Y. Further, as shown in FIGS. 5 and 8, the cap 21 is configured to be larger than the syringe body 20 in the radial direction. Thus, a proximal end portion (not numbered) of the cap 21 is arranged on an outer side in the radial direction of the syringe body 20. In the present embodiment, the cap 21 is configured as a large-diameter portion (not numbered). The large-diameter portion is configured to have a diameter larger than the trunk portion 200. The large-diameter portion is arranged at the distal end of the trunk portion 200. Thus, the large-diameter portion is arranged on the other side in the axis direction Y of the abutting portion 201 as the vicinity portion of the flange portion 22.

The cap 21 includes a tubular needle protection portion (not numbered) which covers the injection needle 204 from an outer diameter side and a cap body (not numbered) which protects at least the injection needle 204 from the other side in the axis direction Y. The cap body is attached to the needle protection portion. An outer diameter of the needle protection portion is larger than the outer diameter of the trunk portion 200. The needle protection portion is attached to the periphery tube portion 203 and is thereby arranged at the distal end of the trunk portion 200. The needle protection portion and the syringe body 20 move relative to each other in the axis direction Y, and thereby the needle protection portion is shifted from a state where the injection needle 204 is housed in the needle protection portion to a state where the injection needle 204 is protruded from the needle protection portion. Thus, in the state where the injection needle 204 is housed, the needle protection portion prevents the injection needle 204 from being unintentionally stuck into skin or the like of a person. The cap body is configured to have a bottomed tubular shape. An inner diameter of the cap body is larger than the outer diameter of the needle protection portion. In the present embodiment, in a state before use, the needle protection portion is inserted in the cap body. Accordingly, the injection needle 204 is prevented from protruding from the needle protection portion.

As shown in FIGS. 1 and 5 to 7, the flange portion 22 protrudes from the outer periphery surface of the syringe body 20 to an outer side in the radial direction. Thus, the flange portion 22 has a diameter larger than the syringe body 20. The flange portion 22 of the present embodiment is provided in the radial direction. Further, the flange portion 22 is arranged on the proximal end side of the cap 21. The flange portion 22 of the present embodiment is provided at the proximal end of the trunk portion 200. Thus, the flange portion 22 is shorter than the syringe body 20 in the axis direction Y. As shown in FIG. 5, the flange portion 22 includes a flange distal end portion 220 which is arranged on a distal end side, a flange edge portion 221 which is arranged on the one side in the axis direction Y of the flange distal end portion 220, and a flange proximal end portion (not numbered) which is arranged on a proximal end side. In addition, the flange portion 22 of the present embodiment is provided in a whole area in the circumferential direction. Thus, the flange distal end portion 220 and the flange proximal end portion are configured to have planar shapes which extend in the radial direction and the circumferential direction. The flange edge portion 221 is arranged on an outer side of the syringe 2 in the radial direction of the flange distal end portion 220 and the flange proximal end portion. As shown in FIG. 1, the flange portion 22 of the present embodiment is configured to be longer in the lateral direction X than in the vertical direction Z. As shown in FIG. 5, the flange portion 22 has a diameter larger than the cap 21. Further, the flange portion 22 is arranged on the proximal end side of the trunk portion 200 relative to the cap 21 which is configured as the large-diameter portion.

As shown in FIG. 1, the syringe housing container 3 includes a syringe holder 5 for holding the syringe 2 and a container body 8 which houses the syringe holder 5.

The syringe holder 5 includes a holding body 6 and a periphery portion 7.

In the syringe holder 5, the holding body 6 is a portion for holding the syringe 2. The holding body 6 includes a base plate portion 60 and the tube portions 61.

Figure 2:
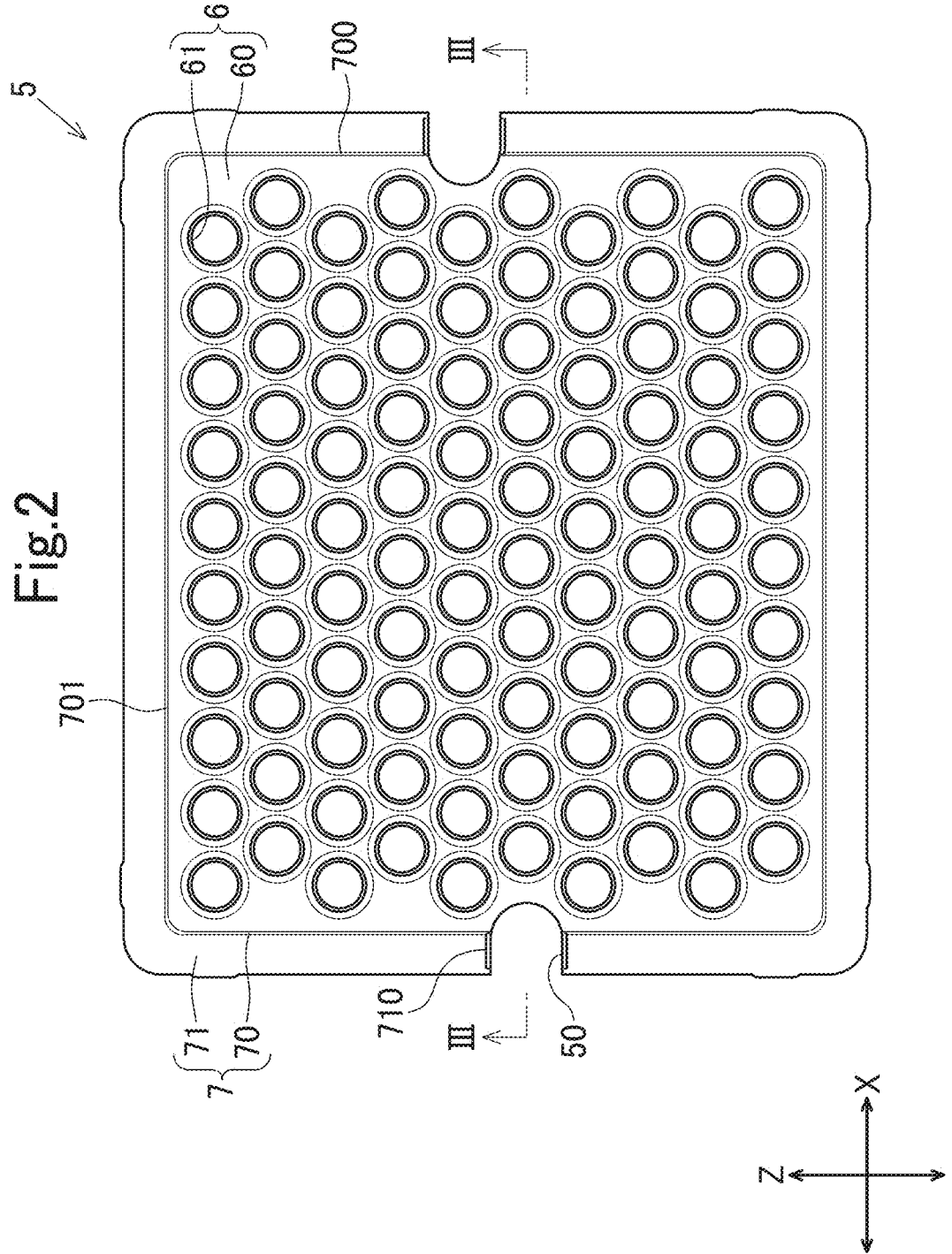
FIG. 2 is a plan view of a syringe holder according to the embodiment.
Figure 3:
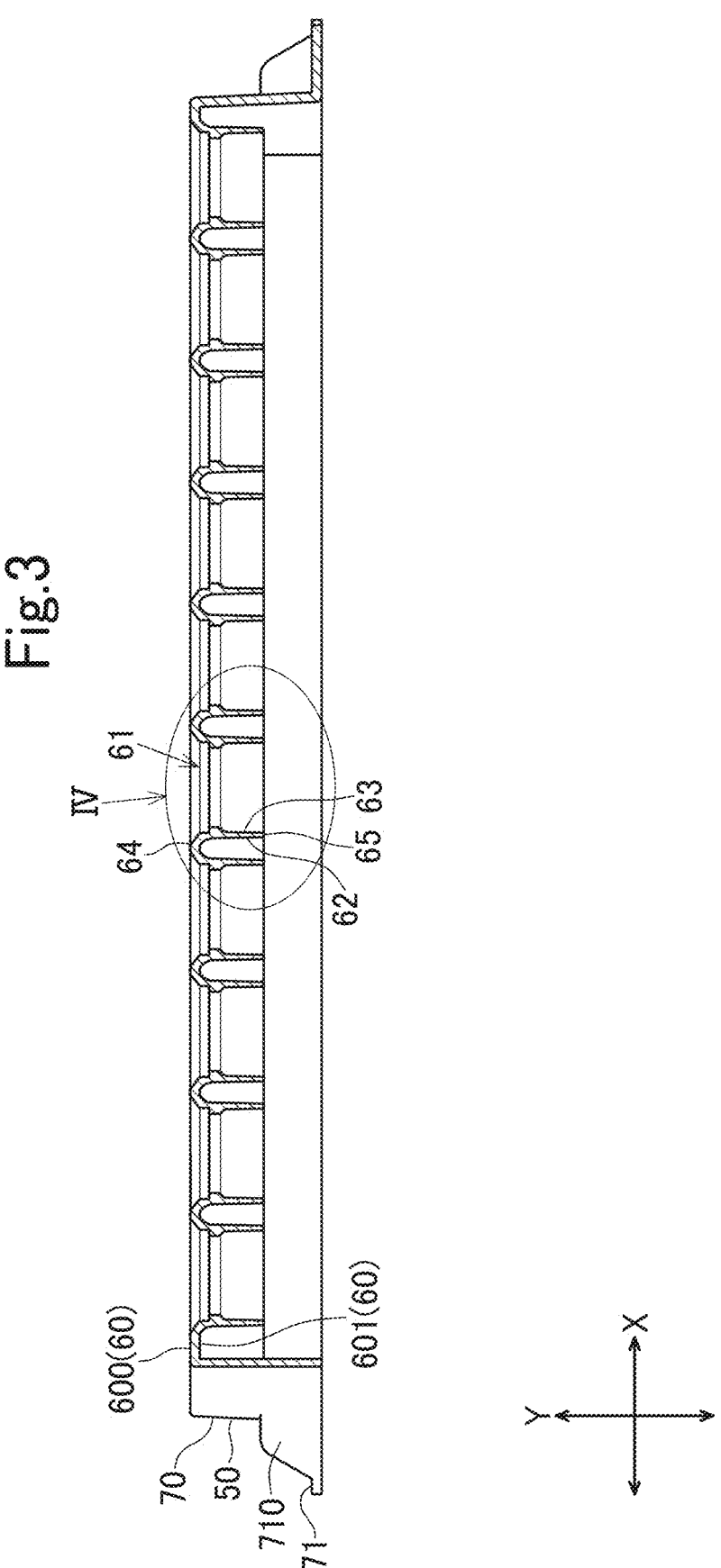
FIG. 3 is a cross-sectional view, which is taken in a III-III direction, of the syringe holder according to the embodiment.

The base plate portion 60 is formed into a plate shape (specifically, a flat plate shape). The base plate portion 60 shown in FIGS. 1 and 3 is arranged in a state where a plate thickness direction coincides with the axis direction Y. As shown in FIG. 3, the base plate portion 60 has a front surface 600 and a back surface 601. The base plate portion 60 of the present embodiment is a rectangular plate which extends in the vertical direction Z and the lateral direction X. Specifically, as shown in FIG. 2, the base plate portion 60 is configured to have short sides in the vertical direction Z and long sides in the lateral direction X.

The tube portion 61 is a portion through which the syringe 2 is inserted. Thus, the tube portion 61 is configured to have a tubular shape (specifically, a cylindrical shape) having a diameter larger than the syringe 2. Further, as shown in FIG. 5, the tube portion 61 of the present embodiment is shorter than the syringe 2 in the axis direction Y.

The tube portion 61 is arranged to pass through the base plate portion 60 in the plate thickness direction. That is, as shown in FIG. 3, in a state where the axis direction Y is caused to coincide with the plate thickness direction of the base plate portion 60, the tube portion 61 of the present embodiment extends in the axis direction Y from one surface (specifically, the front surface 600) of the base plate portion 60 in the plate thickness direction and protrudes from the other surface (specifically, the back surface 601). Thus, a length of the tube portion 61 of the present embodiment in the axis direction Y is longer than a length of the base plate portion 60 in the plate thickness direction.

Figure 10:
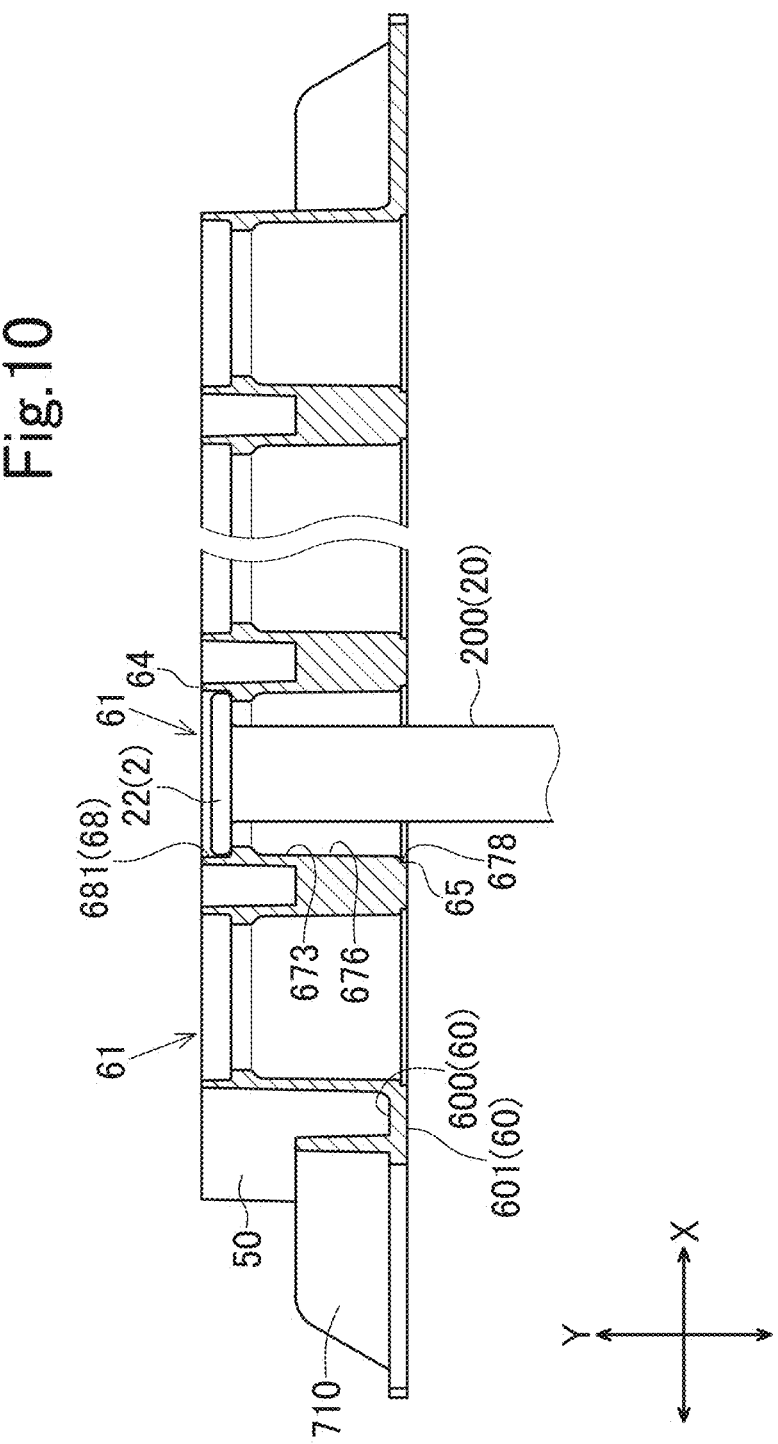
FIG. 10 is a lateral cross-sectional view of the syringe holder shown in FIG. 9.

In the present embodiment, a plurality of tube portions 61 are arranged in the base plate portion 60. Specifically, as shown in FIGS. 2 and 3, 10 tube portions 61 are arranged in the lateral direction X. Further, while the 10 tube portions 61 are set as one column, 10 columns are aligned in the vertical direction Z. Thus, 100 tube portions 61 are arranged in the base plate portion 60. Accordingly, the syringe holder of the present embodiment is capable of holding a plurality of syringes 2. In the present embodiment, all of the tube portions 61 are in the same configuration. Thus, in the following, a description will be made about one tube portion 61 among the plurality of tube portions 61, and the description applies to the other tube portions 61.

It is assumed that the column of the tube portions 61 which is positioned on the lowest side in the vertical direction Z in FIG. 2 is set as a first column and the columns are aligned, upward in the vertical direction Z, as a second column, a third column, . . . in the vertical direction Z. In the second column of the present embodiment, the tube portion 61 positioned at a left end is arranged on a left side relative to the tube portion 61 positioned at a left end in the first column. Specifically, the tube portion 61 at the left end of the second column is arranged on the left side from the tube portion 61 at the left end of the first column by half a distance, which corresponds to half a distance between centers of the tube portions 61 adjacent to each other in the lateral direction X. In the present embodiment, the tube portion 61 at the left end of each of even columns among the first to tenth columns is arranged on the left side by half the distance relative to the tube portion 61 at the left end of each of odd columns. On the other hand, the tube portion 61 at a right end of each of the odd columns is arranged on a right side by half the distance relative to the tube portion 61 at a right end of each of the even columns. As shown in FIG. 2, in the present embodiment, the tube portions 61 in the columns adjacent to each other in the vertical direction Z are arranged in a staggered manner. Further, in the present embodiment, hexagonal lattice arrangement is employed in which one tube portion 61 is surrounded by six tube portions 61. Furthermore, with respect to one tube portion 61, a separation distance from each of left and right tube portions 61 and 61, a separation distance from each of obliquely right and obliquely left tube portions 61 and 61 in the column higher by one column, and a separation distance from each of obliquely right and obliquely left tube portions 61 and 61 in the column lower by one column are equivalent.

As described above, the tube portion 61 has a tubular shape. Thus, as shown in FIG. 3, the tube portion 61 includes an outer wall surface 62 which constitutes an outer periphery surface, an inner wall surface 63 which constitutes an inner periphery surface, one end 64 which is arranged on the one side in the axis direction Y, and another end 65 which is continuous with the outer wall surface 62 and the inner wall surface 63 on the other side in the axis direction Y.

Figure 4:
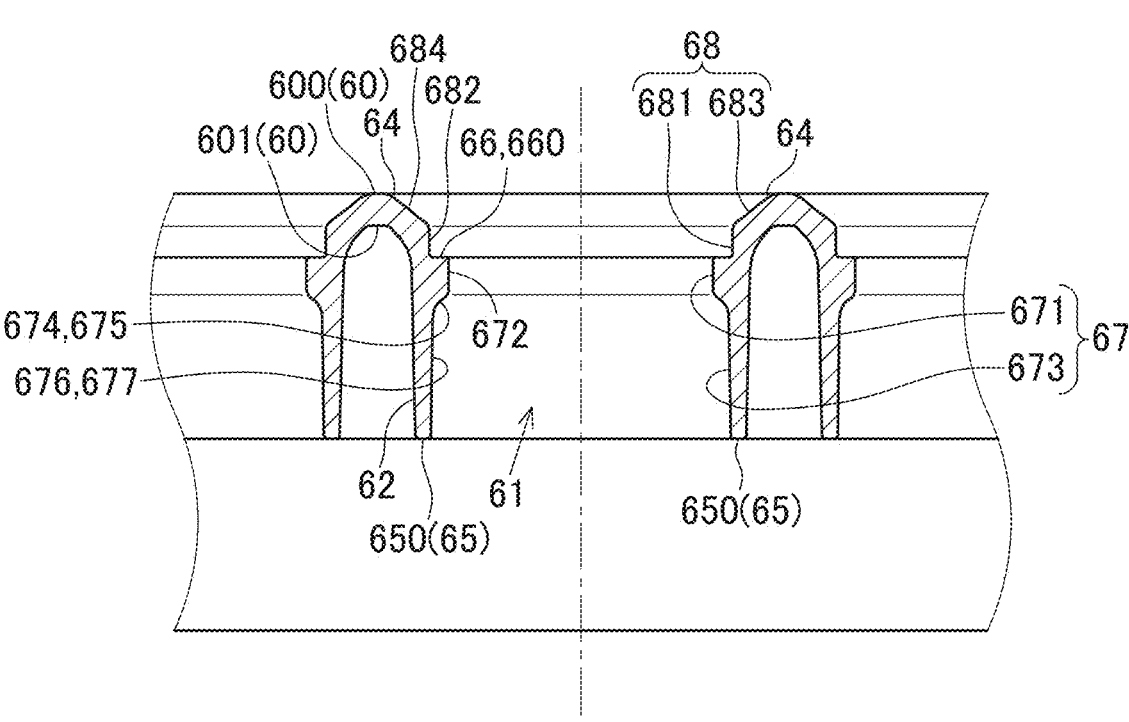
FIG. 4 is an enlarged cross-sectional view of the syringe holder according to the embodiment in a surrounded section IV in FIG. 3.
Figure 4:
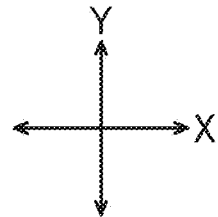

The outer wall surface 62 forms the outer periphery surface of the tube portion 61. As shown in FIGS. 3 and 4, the outer wall surface 62 extends from the back surface 601 of the base plate portion 60 to the other side in the axis direction Y. The outer wall surface 62 is continuous with the back surface 601 of the base plate portion 60 and the other end 65. The outer wall surface 62 of the present embodiment is a tapered surface in which an outer diameter of the tube portion 61 becomes smaller toward the other side in the axis direction Y. The outer wall surface 62 extends in a circumferential direction of the tube portion 61. Thus, the outer wall surface 62 is a surface which extends in the axis direction Y and the circumferential direction. A length of the outer wall surface 62 of the present embodiment in the axis direction Y is longer than the length of the base plate portion 60 in the plate thickness direction.

As shown in FIG. 3, the inner wall surface 63 extends between the one end 64 and the other end 65 in the inner periphery surface of the tube portion 61. The inner wall surface 63 is longer than the outer wall surface 62 in the axis direction Y. As shown in FIG. 4, the inner wall surface 63 (not provided with the reference numeral in FIG. 4) includes a flange support portion 66, a side wall portion 67 which is arranged on the other side in the axis direction Y relative to the flange support portion 66, and a rising wall portion 68 which is arranged on the one side in the axis direction Y relative to the flange support portion 66.

As shown in FIG. 5, the flange support portion 66 supports the flange portion 22 from the other side in the axis direction Y. The flange support portion 66 has a support surface 660 which extends in the radial direction. As shown in FIGS. 4 and 5, the support surface 660 of the present embodiment extends in the radial direction. Further, the support surface 660 of the present embodiment extends in the circumferential direction. Thus, the support surface 660 of the present embodiment is a surface which extends in the radial direction and the circumferential direction. In addition, the support surface 660 of the present embodiment extends in a whole circumference in the circumferential direction. Thus, the flange support portion 66 is arranged throughout the whole circumference in the circumferential direction. The flange support portion 66 of the present embodiment is arranged on the other side in the axis direction Y relative to the back surface 601 of the base plate portion 60.

The side wall portion 67 is formed on the other side in the axis direction Y relative to the flange support portion 66. As shown in FIG. 4, the side wall portion 67 of the present embodiment is continuous with the flange support portion 66 and the other end 65. As shown in FIG. 5, the side wall portion 67 is shorter than the syringe body 20 in the axis direction Y. The side wall portion 67 includes a syringe abutting portion 671 and a side wall body portion 673.

As shown in FIG. 7, when the syringe 2 is inserted through an inside of the tube portion 61, the syringe abutting portion 671 abuts the syringe body 20 from an outer side in the radial direction. The syringe abutting portion 671 has a syringe abutting surface 672. The syringe abutting surface 672 of the present embodiment extends in the axis direction Y. The syringe abutting surface 672 extends in the circumferential direction. Thus, the syringe abutting surface 672 is a surface (specifically, a flat surface) which extends in the axis direction Y and the circumferential direction. The syringe abutting surface 672 of the present embodiment extends in the whole area in the circumferential direction. Accordingly, the syringe abutting portion 671 is arranged throughout the whole area in the circumferential direction. The syringe abutting portion 671 is arranged on an inner side in the radial direction relative to the flange support portion 66. As shown in FIGS. 4 and 7, in the present embodiment, the syringe abutting surface 672 is continuous from an end of the support surface 660 on a radially inner side, the support surface 660 extending in the radial direction, to the other side in the axis direction Y. Thus, the syringe abutting portion 671 is continuous with the flange support portion 66. An inner diameter of the syringe abutting portion 671 is shortest in the tube portion 61. As shown in FIG. 5, the inner diameter of the syringe abutting portion 671 is larger than the cap 21. On the other hand, the inner diameter of syringe abutting portion 671 is smaller than the flange portion 22.

As shown in FIG. 4, the side wall body portion 673 is arranged on the other side in the axis direction Y relative to the syringe abutting portion 671. The side wall body portion 673 of the present embodiment is arranged on a radially outer side relative to the syringe abutting portion 671.

Further, the side wall body portion 673 of the present embodiment is longer than the syringe abutting portion 671 in the axis direction Y.

The side wall body portion 673 includes a large-diameter guide portion 674 which guides the large-diameter portion (in the present embodiment, the cap 21) to an inner side in the radial direction and a side wall other-side portion 676.

The large-diameter guide portion 674 is for guiding the large-diameter portion to the inner side in the radial direction when for example, in order to pull the syringe 2 from the tube portion 61, the syringe 2 inserted through the tube portion 61 is moved from the other side to the one side in the axis direction Y. As shown in FIG. 4, the large-diameter guide portion 674 is configured to have a diameter decreasing from the other side toward the one side in the axis direction Y. The large-diameter guide portion 674 includes a large-diameter guide surface 675. The large-diameter guide surface 675 is an inclined surface in which an inner diameter of the tube portion 61 becomes smaller toward the one side in the axis direction Y. The large-diameter guide surface 675 extends in the circumferential direction. Thus, the large-diameter guide surface 675 is a surface which extends in directions, which intersect with the axis direction Y, and in the circumferential direction such that the inner diameter of the tube portion 61 becomes smaller toward the one side in the axis direction Y. The large-diameter guide surface 675 is continuous from an other-side end of the syringe abutting surface 672 in the axis direction Y to the other side in the axis direction Y. Thus, the large-diameter guide portion 674 and the syringe abutting portion 671 are continuous in the axis direction Y. Accordingly, the large-diameter guide portion 674 is arranged on the other side in the axis direction Y relative to the syringe abutting portion 671.

As shown in FIG. 4, the side wall other-side portion 676 is arranged on the other side in the axis direction Y and on the outer side in the radial direction, relative to the large-diameter guide portion 674. The side wall other-side portion 676 has a side wall other-side surface 677. The side wall other-side surface 677 is continuous with the large-diameter guide surface 675 and the other end 65. The side wall other-side surface 677 extends in the axis direction Y. The side wall other-side surface 677 of the present embodiment is an inclined surface in which the inner diameter of the tube portion 61 becomes larger toward the other side in the axis direction Y. Further, the side wall other-side surface 677 extends in the circumferential direction. Thus, the side wall other-side surface 677 is a surface which extends in the directions, which intersect with the axis direction Y, and in the circumferential direction such that the inner diameter of the tube portion 61 becomes larger toward the other side in the axis direction Y. Further, the side wall other-side surface 677 of the present embodiment is longer than the syringe abutting surface 672 in the axis direction Y.

As shown in FIG. 4, the rising wall portion 68 extends from the flange support portion 66 to the one end 64. The rising wall portion 68 of the present embodiment is shorter than the side wall portion 67 in the axis direction Y. The rising wall portion 68 includes a flange abutting portion 681 and a flange guide portion 683.

As shown in FIG. 4, the flange abutting portion 681 is arranged on the one side in the axis direction Y relative to the flange support portion 66. Further, the flange abutting portion 681 is arranged on the outer side in the radial direction relative to the flange support portion 66. As shown in FIG. 5, the flange abutting portion 681 is capable of abutting, from the outer side in the radial direction, the flange portion 22 (specifically, the flange edge portion 221)

which is supported by the flange support portion 66. The flange abutting portion 681 includes a flange abutting surface 682. The flange abutting surface 682 extends in the axis direction Y. The flange abutting surface 682 extends in the circumferential direction. Thus, the flange abutting surface 682 is a surface which extends in the axis direction Y and the circumferential direction. In the present embodiment, the flange abutting surface 682 is arranged in the whole area in the circumferential direction. As described above, the flange abutting portion 681 is arranged on the outer side in the radial direction relative to the flange support portion 66. Further, in the present embodiment, the flange abutting surface 682 of the flange abutting portion 681 is continuous from an end of the support surface 660 on a radially outer side, the support surface 660 extending in the radial direction, to the one side in the axis direction Y. Thus, an inner diameter of the flange abutting portion 681 is larger than the inner diameter of the syringe abutting portion 671. Further, the inner diameter of the flange abutting portion 681 is larger than the flange portion 22. In the present embodiment, a configuration is made such that a length of the flange abutting surface 682 in the axis direction Y is substantially the same as a length of the flange portion 22 in the axis direction Y.

The flange guide portion 683 is arranged on the one side in the axis direction Y relative to the flange abutting portion 681. Further, the flange guide portion 683 is arranged on the outer side in the radial direction relative to the flange abutting portion 681. The flange guide portion 683 has a flange guide surface 684. The flange guide surface 684 is an inclined surface in which the inner diameter of the tube portion 61 becomes smaller toward the other side in the axis direction Y. Accordingly, the flange guide portion 683 is configured to have a diameter gradually decreasing from the one side toward the other side in the axis direction Y. Incidentally, as shown in FIG. 7, in a case where the syringe abutting portion 671 abuts the abutting portion 201 on the other side in the axis direction Y relative to the flange portion 22, it is necessary to cause the flange portion 22 not to run onto the front surface 600 of the base plate portion 60. Thus, in the present embodiment, lengths of the flange guide surface 684 and the support surface 660 in the radial direction are longer than a protruding length of the flange portion 22 with respect to the outer periphery surface of the syringe body 20. In addition, the flange guide surface 684 extends in the circumferential direction. Thus, the flange guide surface 684 is a surface which extends in the directions, which intersect with the axis direction Y, and in the circumferential direction such that the inner diameter of the tube portion 61 becomes smaller toward the other side in the axis direction Y. The flange guide surface 684 of the present embodiment extends in the whole area in the circumferential direction. Thus, the flange guide portion 683 is formed throughout the whole area in the circumferential direction. As shown in FIG. 4, the flange guide surface 684 is continuous with the one end 64 and the flange abutting surface 682. Accordingly, an inner diameter of the flange guide portion 683 is larger than the inner diameter of the flange abutting portion 681. Note that the inner diameter of the flange guide portion 683 is larger than the flange portion 22.

As shown in FIG. 4, the one end 64 is a ridge portion between the rising wall portion 68 (specifically, the flange abutting surface 682) and the front surface 600 of the base plate portion 60. The one end 64 extends in the circumferential direction. In the present embodiment, an inner diameter of the one end 64 is largest in the tube portion 61.

As shown in FIG. 4, the other end 65 is continuous with the outer wall surface 62 and the side wall other-side portion 676 in the radial direction. The other end 65 has an other-end surface 650. The other-end surface 650 is a surface which extends in the radial direction and the circumferential direction. The other-end surface 650 of the present embodiment extends in the radial direction. The other end 65 of the present embodiment is arranged on the radially inner side relative to the one end 64.

As shown in FIGS. 1 and 2, the periphery portion 7 is for raising the holding body 6 in the axis direction Y. The periphery portion 7 includes a step portion 70 and a placing portion 71.

As shown in FIG. 1, the step portion 70 is provided to extend from the base plate portion 60 to the other side in the axis direction Y. The step portion 70 is longer than the tube portion 61 in the axis direction Y. As shown in FIG. 2, the step portion 70 of the present embodiment is provided in a whole area of the base plate portion 60 in the lateral direction X and the vertical direction Z. The step portion 70 includes a pair of vertical step portions 700 and 700 which are opposed to each other in the lateral direction X and a pair of lateral step portions 701 and 701 which are opposed to each other in the vertical direction Z. In the present embodiment, the pair of vertical step portions 700 and 700 are coupled with the pair of lateral step portions 701 and 701, and the step portion 70 is thereby formed throughout a whole area of the base plate portion 60 in the circumferential direction.

The placing portion 71 is for placing the syringe holder 5 on the container body 8. As shown in FIG. 1, the placing portion 71 is provided to extend from the step portion 70 to the other side in the axis direction Y. The placing portion 71 protrudes from the step portion 70 to the outer side in the radial direction. As shown in FIG. 2, the placing portion 71 of the present embodiment is arranged in a whole area in the circumferential direction. The placing portion 71 has a front surface (not numbered) and a back surface (not numbered) in the plate thickness direction, and the back surface is placed on a side wall step portion 814 in the container body 8, which will be described later.

In the syringe holder 5 of the present embodiment, a pair of cutouts 50 are formed in opposed sides. In a state where the syringe holder 5 is housed in the container body 8, a finger or a hook is locked in a back surface of the syringe holder 5, and the cutouts 50 are thereby used when the syringe holder 5 is taken out from the container body 8. As shown in FIG. 2, in the present embodiment, on both sides in the lateral direction X, the cutouts 50 are formed which cutout the base plate portion 60 and the periphery portion 7.

As shown in FIGS. 1 to 3, the placing portion 71 is provided with extension portions 710 which extend outward from the front surface. Each of the extension portions 710 extends outward from a peripheral edge of the cutout 50 formed in the front surface to the one side in the axis direction Y.

As shown in FIG. 1, the container body 8 is a container having a bottomed tubular shape. The container body 8 of the present embodiment includes a plate-shaped bottom portion 80 and a side wall portion 81 provided to extend from a peripheral edge of the bottom portion 80. The bottom portion 80 of the present embodiment is a rectangular plate-shaped member which has long sides and short sides. The side wall portion 81 includes a pair of width side wall portions 810 which are opposed to each other in a longitudinal direction of the bottom portion 80 (specifically, the lateral direction X) and a pair of longitudinal side wall portions 811 which are opposed to each other in a short-side direction of the bottom portion 80 (specifically, the vertical direction Z). Both end portions of the pair of width side wall portions 810 in the longitudinal direction are coupled with both end portions of the pair of longitudinal side wall portions 811 in the short-side direction. Accordingly, the side wall portion 81 is formed which is provided throughout the peripheral edge of the bottom portion 80.

The side wall portion 81 has a lower-section side wall portion 812 which forms an opening region having substantially the same area as an area of the bottom portion 80 and an upper-section side wall portion 813 which forms an opening region wider than the opening region of the lower-section side wall portion 812. The lower-section side wall portion 812 is continuous with the peripheral edge of the bottom portion 80. An opening end edge of the upper-section side wall portion 813 serves as a brim portion 815 which is formed in a brim shape. At a boundary between the lower-section side wall portion 812 and the upper-section side wall portion 813, the side wall portion 81 has a side wall step portion 814 for extending the opening region of the lower-section side wall portion 812 to the opening region of the upper-section side wall portion 813. Note that a length of the upper-section side wall portion 813 of the present embodiment in the axis direction Y is longer than a length of the syringe holder 5 in the axis direction Y.

The protection film 4 is for tightly sealing an internal portion of the container body 8 by covering an opening of the container body 8. Thus, the protection film 4 is larger than the opening of the container body 8 in the lateral direction X and the vertical direction Z. The protection film 4 is used by being stuck to the brim portion 815 of the upper-section side wall portion 813. The protection film 4 of the present embodiment is stuck to the brim portion 815 by heat sealing. The protection film 4 is formed with a non-woven fabric which has gas permeability and microbe impermeability. Thus, the protection film 4 is configured such that sterilization gas is permeable. Further, the protection film 4 is configured not to allow microbes or bacteria to enter the internal portion of the container body 8.

The protection cover is for not allowing dirt to enter the inside of the trunk portion 200. The protection cover is used by covering the proximal end of the trunk portion 200. Note that the protection cover is made of a gas-permeable non-woven fabric through which sterilization gas is permeable.

The sterilization bag is for housing the container body 8. The sterilization bag has gas permeability and microbe impermeability. Thus, the sterilization bag is configured such that sterilization gas is permeable. Further, the sterilization bag is configured not to allow microbes or bacteria to enter an inside of the sterilization bag.

Next, a description will be made about a method of assembling the package 1.

First, the syringe 2 is inserted through the tube portion 61. Accordingly, the syringe 2 is held by the syringe holder 5. Specifically, as shown in FIG. 1, in a state where the syringe 2 is arranged on the one side in the axis direction Y relative to the syringe holder 5, a distal end side of the syringe 2 is directed to the other side in the axis direction Y. Then, a central axis of the syringe 2 and a central axis of the tube portion 61 are caused to coincide with each other.

Subsequently, the syringe 2 is inserted through the tube portion 61. Here, the inner diameters of the flange guide portion 683 and the flange abutting portion 681 are larger than the flange portion 22. Thus, the syringe 2 can be inserted into the tube portion 61 from the one side in the axis direction Y. In this case, due to the flange guide surface 684 which is configured as the inclined surface in which the inner diameter of the tube portion 61 becomes smaller toward the other side in the axis direction Y, the flange guide portion 683 have a diameter gradually decreasing from the one side toward the other side in the axis direction Y. Thus, the syringe 2 is easily inserted into the tube portion 61. Further, the inner diameter of the syringe abutting portion 671, which is smallest in the tube portion 61, is larger than the cap 21. Thus, the cap 21 and the syringe body 20 can be advanced to the other side in the axis direction Y relative to the flange support portion 66, and the syringe 2 can be inserted through the tube portion 61. On the other hand, the inner diameter of the syringe abutting portion 671 is smaller than the flange portion 22. Thus, when the syringe 2 is advanced to the other side in the axis direction Y in the tube portion 61, the flange distal end portion 220 is placed on the support surface 660 from the other side of the flange distal end portion 220 in the axis direction Y. Accordingly, the flange portion 22 is supported by the flange support portion 66. Consequently, the syringe 2 is held by the syringe holder 5. In the present embodiment, the syringes 2 are inserted through all of the tube portions 61.

Next, as shown in FIG. 1, the syringe holder 5 is arranged such that the lateral direction X of the syringe holder 5 holding the syringes 2 coincides with the longitudinal direction of the container body 8, and the back surface of the placing portion 71 is placed on the side wall step portion 814. Accordingly, the syringe holder is housed in the container body 8. Here, in the present embodiment, the length of the upper-section side wall portion 813 in the axis direction Y is longer than the length of the syringe holder 5 in the axis direction Y. Thus, as shown in FIG. 5, the placing portion 71 is placed on the side wall step portion 814, and the syringe holder 5 is thereby housed in the container body 8. Further, in the present embodiment, in a state where the placing portion 71 is placed on the side wall step portion 814 and the syringe holder 5 is housed in the container body 8, a separation distance between the flange support portion 66 and the bottom portion 80 in the axis direction Y is longer than a length from the flange distal end portion 220 to the distal end of the syringe 2. Accordingly, when the syringe holder 5 is housed in the container body 8, the distal end of the syringe 2 is prevented from abutting the bottom portion 80, and the flange portion 22 can thereby be prevented from being separated from the flange support portion 66.

Subsequently, in order not to allow dirt to enter the inside of the trunk portion 200 from the proximal end of the trunk portion 200, the syringe 2 is covered by the protection cover. Specifically, in the container body 8, the protection cover is put on the front surface 600 of the base plate portion 60 and covers the syringes 2 inserted through all of the tube portions 61.

Then, in order to tightly seal the internal portion of the container body 8, the protection film 4 is stuck to the container body 8. In this case, as shown in FIG. 5, from the one side in the axis direction Y, the protection film 4 is stuck to the brim portion 815. Accordingly, the opening of the container body 8 is covered by the protection film 4, and the inside of the container body 8 is tightly sealed. Here, in the present embodiment, the length of the upper-section side wall portion 813 in the axis direction Y is longer than the length of the syringe holder 5 in the axis direction Y. Thus, when the placing portion 71 is placed on the side wall step portion 814, the syringe holder 5 is housed in the container body 8. Accordingly, when the protection film 4 is stuck, interference between the syringe holder 5 and the protection film 4 can be prevented. In a state where the internal portion of the container body 8 is tightly sealed, the container body 8, the syringe holder 5, the syringes 2, the protection cover, and the protection film 4 are arranged in this order from the other side to the one side in the axis direction Y.

After the protection film 4 is stuck to the container body 8, the container body 8 is housed in the sterilization bag. Then, the sterilization bag which houses the container body 8 is tightly sealed. In such a manner, the package 1 is assembled. Further, in the present embodiment, the assembled package 1 is subjected to a sterilization treatment by a γ ray for sterilization of microbes and bacteria. Here, the sterilization bag, the protection film 4, and the protection cover have gas permeability. Thus, instead of the γ ray, the sterilization treatment may be performed with sterilization gas. In this case, the sterilization gas permeates the sterilization bag, the protection film 4, and the protection cover, and an inside of the container body 8 is thereby sterilized.

The syringe holder 5 of the present embodiment includes the plate-shaped base plate portion 60 and the tube portion 61 being formed into a tubular shape having the axis direction Y being provided along the plate thickness direction of the base plate portion 60, the tube portion 61 being configured to allow the syringe 2 to be inserted through the tube portion 61 from the one side toward the other side in the axis direction Y, the syringe 2 including the tubular syringe body 20 and the flange portion 22 protruding from the outer periphery surface of the syringe body 20 to the outer side in the radial direction. The tube portion 61 includes the inner wall surface 63 through which the syringe 2 is inserted, the flange support portion 66 having the support surface 660 which is positioned on the inner side of the inner wall surface 63 in the radial direction and extends in the radial direction, the flange support portion 66 being configured to abut the flange portion 22 of the inserted syringe 2 from the other side in the axis direction Y and supporting the flange portion 22 in the axis direction Y, and the flange abutting portion 681 being arranged on the one side in the axis direction Y relative to the flange support portion 66 and on the outer side in the radial direction relative to the support surface 660 and having the flange abutting surface 682 which extends in the axis direction Y, the flange abutting portion 681 being configured to abut the flange portion 22 supported by the flange support portion 66 from the outer side in the radial direction and to support the flange portion 22 in the radial direction.

In the syringe holder 5 in the above configuration, in a state where the syringe 2 is inserted through the tube portion 61, the flange support portion 66 supports the flange portion 22 of the syringe 2 from the other side in the axis direction Y, and the syringe 2 can thereby be supported. The flange abutting portion 681, which is arranged on the one side in the axis direction Y and on the outer side in the radial direction, relative to the flange support portion 66, abuts the flange portion 22 in the radial direction, movement of the syringe 2 in the radial direction can thereby be regulated, and displacement of the syringe 2 with respect to the tube portion 61 can thus be inhibited.

Further, in the syringe holder 5 of the present embodiment, the tube portion 61 includes the syringe abutting portion 671, and the syringe abutting portion 671 is arranged on the other side in the axis direction Y relative to the flange support portion 66 and on the inner side in the radial direction relative to the support surface 660 and has the syringe abutting surface 672 which extends in the axis direction Y, and the syringe abutting portion 671 is configured to be capable of abutting, from the outer side in the radial direction, a portion of the syringe body 20, the portion being in vicinity to the flange portion 22 in the syringe body 20 on the other side in the axis direction Y relative to the flange portion 22.

In the syringe holder 5 in the above configuration, the syringe abutting portion 671, which is arranged on the other side in the axis direction Y and on the inner side in the radial direction, relative to the flange support portion 66, is configured to be capable of abutting the portion of the syringe body 20, the portion being in vicinity to the flange portion 22 in the syringe body 20 on the other side in the axis direction Y relative to the flange portion 22. Thus, when the syringe 2 inserted through the tube portion 61 moves in the tube portion 61, the syringe abutting portion 671 abuts the portion close to the flange portion 22 in the syringe body 20. Consequently, even if the syringe body is scratched by abutting the syringe abutting portion 671, because a scratch is formed in the portion in vicinity to the flange portion 22, the scratch is formed in an inconspicuous part.

Further, in the syringe holder 5 of the present embodiment, the syringe body 20 includes the tubular trunk portion 200 which stores a solution, the syringe 2 includes the large-diameter portion arranged in the distal end portion of the trunk portion 200 and configured to be larger than the trunk portion 200 in the radial direction, the tube portion 61 includes the large-diameter guide portion 674 which guides the large-diameter portion to the inner side in the radial direction, and the large-diameter guide portion 674 is arranged on the other side in the axis direction Y relative to the syringe abutting portion 671 and is configured to have a diameter decreasing from the other side toward the one side in the axis direction Y.

In the syringe holder 5 in the above configuration, the large-diameter guide portion 674, which is arranged on the other side in the axis direction Y relative to the syringe abutting portion 671, is configured to have a diameter decreasing from the other side toward the one side in the axis direction Y. Thus, for example, when the syringe 2 is pulled from the tube portion 61, the large-diameter portion configured to be larger than the trunk portion 200 in the radial direction is guided to the inner side in the radial direction by the large-diameter guide portion 674 which has a diameter gradually decreasing, and the large-diameter portion can thereby be inhibited from being stuck on the other side of the syringe abutting portion 671 in the axis direction Y. Accordingly, the syringe 2 can smoothly be pulled from the tube portion 61.

Further, in the syringe holder 5 of the present embodiment, the tube portion 61 includes the flange guide portion 683 which guides the flange portion 22 to the inner side in the radial direction, the flange guide portion 683 is arranged on the one side in the axis direction Y relative to the flange abutting portion 681 and on the outer side in the radial direction relative to the flange abutting surface 682 of the flange abutting portion 681, has the flange guide surface 684 which extends in the axis direction Y, and is configured to have a diameter decreasing from the one side toward the other side in the axis direction Y.

In the syringe holder 5 in the above configuration, the flange guide portion 683, which is arranged on the one side in the axis direction Y and on the outer side in the radial direction, relative to the flange abutting portion 681, is configured to have a diameter decreasing from the one side toward the other side in the axis direction Y. Thus, for example, even in a case where during transportation of the syringe holder 5 with the syringes 2 inserted through the tube portions 61, the syringe 2 moves due to an impact from the outside and the flange portion 22 deviates from the tube portion 61 to the one side in the axis direction Y, the flange guide portion 683 which has a diameter gradually decreasing guides the flange portion 22 to the inner side in the radial direction, and the flange portion 22 can thereby be settled in the tube portion 61.

Further, the package 1 of the present embodiment includes the above-described syringe holder 5, the syringe 2, and the container body 8 which houses the syringe holder 5.

As shown in FIG. 5, in the present embodiment, in a state where the syringe 2 is inserted through the tube portion 61, the flange distal end portion 220 is placed on the support surface 660. Accordingly, the flange support portion 66 supports the flange portion 22 from the other side in the axis direction Y. Thus, the flange support portion 66 can support the syringe 2. Further, the flange abutting surface 682, which is continuous with the support surface 660, abuts the flange edge portion 221 from the outer side in the radial direction. Accordingly, the flange abutting portion 681, which is arranged on the one side in the axis direction Y and on the outer side in the radial direction, relative to the flange support portion 66, abuts the flange portion 22 in the radial direction. Thus, movement of the syringe 2 in the radial direction can be regulated. Accordingly, displacement of the syringe 2 with respect to the tube portion 61 can be inhibited. Specifically, in the present embodiment, the flange abutting surface 682 is arranged in the whole area in the circumferential direction. Thus, regardless of an orientation of the flange portion 22 in the circumferential direction, the flange abutting portion 681 can abut the flange portion 22 in the radial direction.

Figure 6:
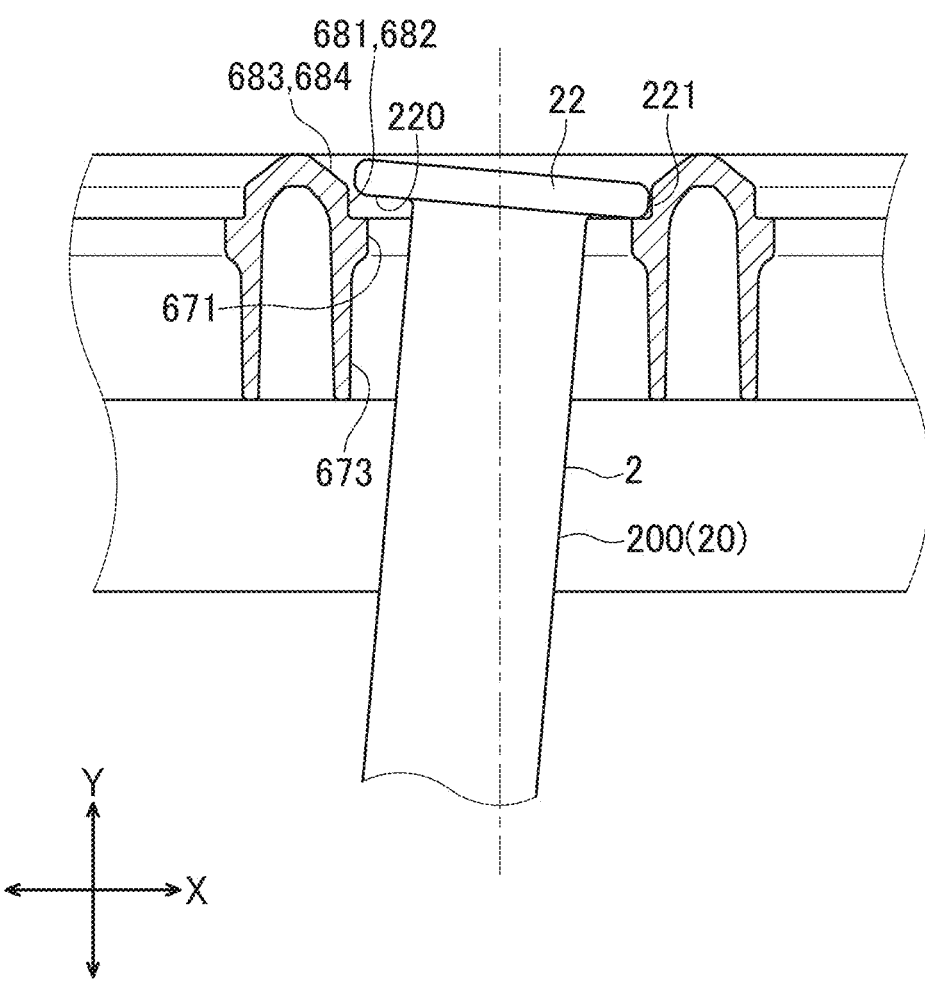
FIG. 6 is an enlarged cross-sectional view of the syringe holder according to the embodiment and is a diagram showing a state where a syringe is shaken.

As shown in FIG. 5, in the present embodiment, in a state where the syringe 2 is inserted through the tube portion 61, a gap between the flange abutting portion 681 and the flange edge portion 221 in the radial direction is smaller than a gap between the syringe body 20 (specifically, the trunk portion 200) and the side wall portion 67 in the radial direction. Thus, for example, when vibration in the radial direction is applied to the syringe holder 5 in a state of holding the syringe 2, the flange abutting portion 681 first abuts flange edge portion 221. Accordingly, by regulating the movement of the syringe 2 in the radial direction, the displacement of the syringe 2 with respect to the tube portion 61 can be inhibited, and the trunk portion 200 and the side wall portion 67 can also be inhibited from abutting each other. As a result, the outer periphery surface of the trunk portion 200 can be inhibited from being scratched. In addition, as shown in FIG. 5, in the present embodiment, in the gap between the syringe body 20 (specifically, the trunk portion 200) and the side wall portion 67 in the radial direction, a gap between the side wall body portion 673 and the trunk portion 200 in the radial direction is larger than a gap between the syringe abutting portion 671 and the trunk portion 200 in the radial direction. Thus, as shown in FIG. 6, for example, when vibration in the radial direction is transmitted to the syringe 2 and a distal end side, in the syringe 2, relative to the flange portion 22 is shaken, the side wall body portion 673 arranged on the other side in the axis direction Y relative to the syringe abutting portion 671 is inhibited from abutting the trunk portion 200, and a scratch can thereby be inhibited from being formed on the distal end side of the trunk portion 200 (specifically, an outer periphery surface of the drug solution filling portion). Accordingly, by inhibiting a scratch from being formed on the outer periphery surface of the drug solution filling portion, the syringe 2 can be inhibited from being determined as a rejected product in a camera inspection for checking that no scratch or defect is present.

Further, in the present embodiment, the tube portion 61 includes the side wall portion 67 which is formed on the other side in the axis direction Y relative to the flange support portion 66. The side wall portion 67 includes the syringe abutting portion 671 which is continuous with the flange support portion 66 and the side wall body portion 673 which is formed on the other side in the axis direction Y relative to the syringe abutting portion 671. The syringe abutting portion 671 is arranged on the inner side in the radial direction relative to the flange support portion 66 and the side wall body portion 673 and is capable of abutting the syringe body 20. Thus, as shown in FIG. 7, for example, in a case where the flange portion 22 deviates to the one side in the axis direction Y and runs onto the flange guide surface 684, the syringe abutting portion 671, which is arranged on the inner side in the radial direction relative to the side wall body portion 673, abuts the abutting portion 201, in the syringe body 20, on the other side in the axis direction Y relative to the flange portion 22. Accordingly, even when the abutting portion 201 abuts the syringe abutting portion 671 and the outer periphery surface of the trunk portion 200 is scratched, a scratch is formed in the abutting portion 201. Consequently, the scratch is formed in an inconspicuous part.

Further, in the present embodiment, the syringe abutting surface 672 is a flat surface. Thus, for example, in a case where the syringe abutting surface 672 abuts the abutting portion 201, a scratch is less likely to be formed in the abutting portion 201.

Further, as shown in FIG. 7, in the present embodiment, the flange guide surface 684, which is continuous with the flange abutting surface 682 of the flange abutting portion 681, is the inclined surface in which the inner diameter of the tube portion 61 becomes smaller toward the other side in the axis direction Y. Thus, for example, in a case where the syringe 2 is inserted through the tube portion 61, the flange distal end portion 220 is separated from the support surface 660 and the flange portion 22 deviates to the one side in the axis direction Y and runs onto the flange guide surface 684, the flange guide portion 683, which has a diameter gradually decreasing from the one side to the other side in the axis direction Y, guides the flange portion 22 to the inner side in the radial direction. Accordingly, the flange portion 22 can be settled in the tube portion 61. That is, when the syringe 2 is advanced from the one side to the other side in the axis direction Y in the tube portion 61, the flange guide portion 683 guides the flange portion 22 to the inner side in the radial direction.

Further, as shown in FIG. 7, in the present embodiment, the lengths of the flange guide surface 684 and the support surface 660 in the radial direction are longer than the protruding length of the flange portion 22 with respect to the outer periphery surface of the syringe body 20. Accordingly, even in a case where the flange portion 22 deviates to the one side in the axis direction Y and the syringe abutting portion 671 and the abutting portion 201 abut each other, the flange portion 22 is arranged on the radially inner side relative to the flange guide surface 684. Thus, the flange portion 22 can be prevented from running onto the front surface 600 of the base plate portion 60, and the flange portion 22 can be settled in the tube portion 61.

Further, in the present embodiment, the tube portion 61 extends from the front surface 600 of the base plate portion 60 in the axis direction Y (specifically, to the other side). Thus, an end portion of the tube portion 61 on the one side in the axis direction Y is connected to the base plate portion 60. Accordingly, a position of the end portion of the tube portion 61 on the one side in the axis direction Y is restrained by the base plate portion 60, and the end portion of each of the tube portions 61 on the one side in the axis direction Y can thereby be positioned. As a result, precision of positioning of the syringe 2 with respect to the tube portion 61 can be enhanced. In addition, as shown in FIG. 5, in the present embodiment, the flange support portion 66 and the flange abutting portion 681 are arranged close to the one side of the tube portion 61 in the axis direction Y. Thus, positioning of the syringe 2 with respect to the tube portion 61 can highly precisely be performed.

Further, in the present embodiment, the step portion 70 is formed throughout the whole area of the base plate portion 60 in the circumferential direction. Thus, the step portion 70 supports the base plate portion 60 from the other side in the axis direction Y in the whole area in the circumferential direction. Accordingly, the base plate portion 60 can be prevented from being tilted.

Further, as shown in FIG. 5, the syringe holder 5 of the present embodiment includes the periphery portion 7 for raising the holding body 6. The periphery portion 7 includes the step portion 70 which is longer than the tube portion 61 in the axis direction Y. Thus, for example, when the placing portion 71 is placed on a desk, the tube portions 61 can be prevented from contacting with the desk.

As described above, as shown in FIG. 5, in a state where the package 1 is assembled, the container body 8, the syringe holder 5, the syringes 2, the protection cover, and the protection film 4 are arranged in this order from the other side to the one side in the axis direction Y. Further, the container body 8 is housed in the sterilization bag. Here, in the sterilization bag, a state where, provided that the axis direction Y is set as a perpendicular direction, the container body 8, the syringe holder 5, the syringes 2, the protection cover, and the protection film 4 are arranged in this order from the other side (specifically, the lower side) to the one side (specifically, the upper side) will be referred to as an upright posture, and a state where the package 1 in the upright posture is inverted will be referred to as the inverted posture. The assembled package 1 is transported in the inverted posture. Specifically, a plurality of packages 1 are housed in a packing box in the inverted posture, and this packing box is transported. Further, the transported package 1 is shifted from the inverted posture to the upright posture at a transportation destination. Then, at the transportation destination, the sterilization bag is unsealed, and the container body 8 is taken out. Then, the protection film 4 is peeled off from the container body 8 which is taken out, the protection cover is removed, and the syringe holder 5 holding the syringes 2 is taken out from the container body 8. Then, the syringe holder 5 holding the syringes 2 is set in a filling device, and the syringes 2 are filled with solutions by the filling device. In the filling device, two punching plates, each of which has a plurality of insertion holes in a plate thickness direction, are superimposed in a state where the respective insertion holes are aligned. Then, in a state where the distal end sides of the syringes 2 held by the syringe holder 5 are inserted through the insertion holes of the punching plates, the syringe holder 5 is placed on the punching plates.

Further, in the present embodiment, the large-diameter guide surface 675 is configured as the inclined surface in which the inner diameter of the tube portion 61 becomes smaller toward the one side in the axis direction Y. Accordingly, the large-diameter guide portion 674 is configured to have a diameter decreasing from the other side toward the one side in the axis direction Y. Thus, as shown in FIG. 8, for example, in a case where the syringe 2 is pulled from the tube portion 61 in a state where the central axis of the tube portion 61 is displaced from the central axis of the syringe 2, the proximal end portion of the cap 21 is guided to the inner side in the radial direction by the large-diameter guide portion 674 even when the proximal end portion of the cap 21 abuts the large-diameter guide portion 674. Accordingly, the cap 21 as the large-diameter portion can be inhibited from being stuck on the one side in the axis direction Y relative to the syringe abutting portion 671. Consequently, the cap 21 can smoothly be pulled from the tube portion 61.

As described above, in the present embodiment, because displacement of the syringe 2 with respect to the tube portion 61 can be inhibited, positioning of the syringe 2 with respect to the tube portion 61 can highly precisely be performed.

The syringe holder and the package according to the present disclosure are not limited to the configurations of the above embodiment. Further, the syringe holder and the package according to the present disclosure are not limited to the above-described work and effects. Various changes are possible for the syringe holder and the package according to the present disclosure without departing from the scope of the gist of the present disclosure.

Figure 9:
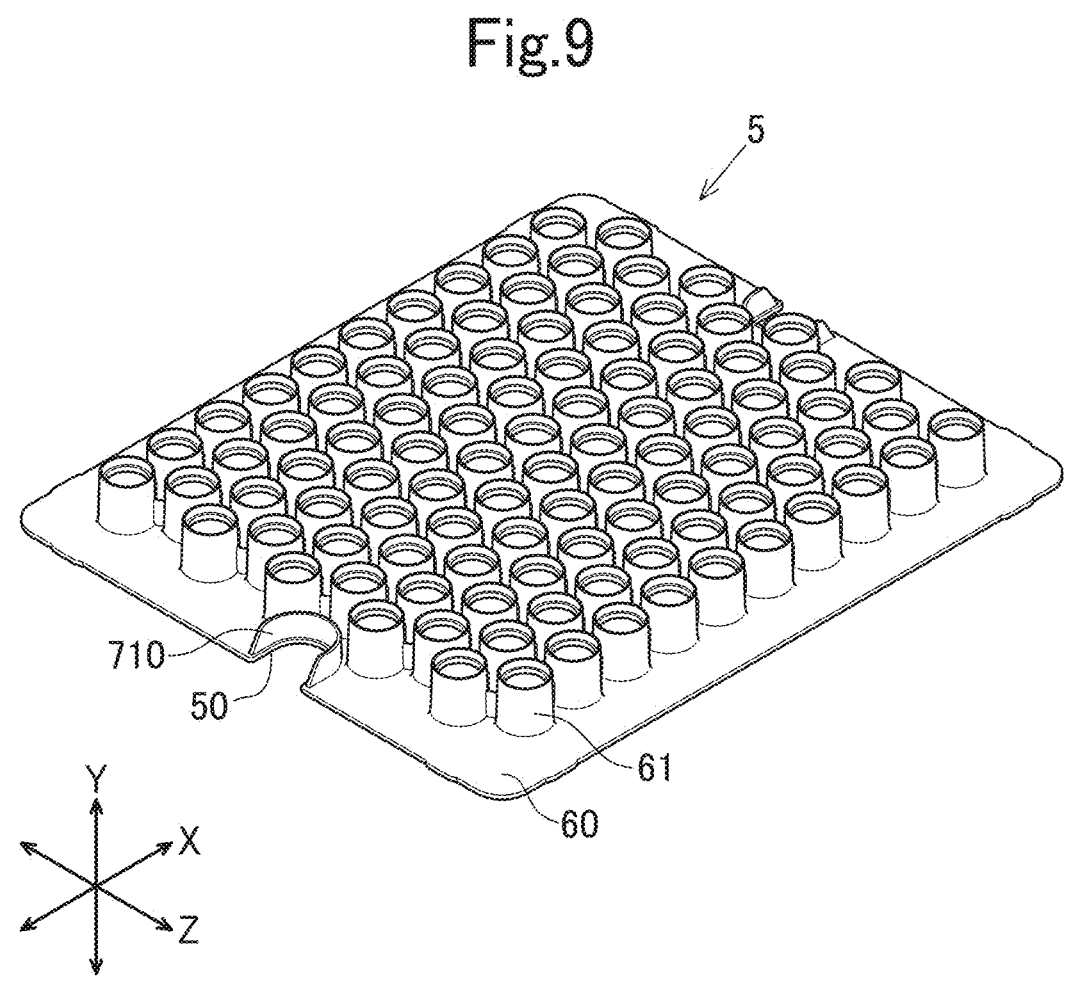

In the above embodiment, a description is made about a case where the tube portion 61 extends in the axis direction Y from one surface (specifically, the front surface 600) of the base plate portion 60 in the plate thickness direction and protrudes from the other surface (specifically, the back surface 601). However, this is not restrictive, and for example, as shown in FIG. 9, each of the tube portions 61 may extend in the axis direction Y from an other-side surface (specifically, the back surface 601) of the base plate portion 60 in the plate thickness direction and may protrude from a one-side surface (specifically, the front surface 600). In this case, the syringe holder 5 does not have to include the periphery portion 7. Further, each of the tube portions 61 may be configured to protrude from the front surface 600 and the back surface 601 of the base plate portion 60 in the plate thickness direction. Alternatively, the length of each of the tube portions 61 in the axis direction Y may be substantially the same as the length of the base plate portion 60 in the plate thickness direction.

As shown in FIGS. 10 to 15, in a case where each of the tube portions 61 extends in the axis direction Y from the other-side surface (specifically, the back surface 601) of the base plate portion 60 in the plate thickness direction and protrudes from the one-side surface (specifically, the front surface 600), the rising wall portion 68 does not have to include the flange guide portion 683. Further, as shown in FIGS. 10 to 15, the side wall body portion 673 may include a side wall proximal end portion 678. The side wall proximal end portion 678 is arranged on the other side in the axis direction Y and on the outer side in the radial direction, relative to the side wall other-side portion 676. The side wall proximal end portion 678 has a side wall proximal end surface (not shown). The side wall proximal end surface extends in the axis direction Y and is continuous with the side wall other-side portion 676 and the other end 65. Further, the side wall proximal end surface extends in a whole area in the circumferential direction. Thus, the side wall proximal end surface extends in the axis direction Y and the circumferential direction. Further, an inner diameter of the side wall proximal end portion 678 is larger than an inner diameter of the side wall other-side portion 676. As shown in FIGS. 10 to 15, a length of the side wall proximal end portion 678 in the axis direction Y may be shorter than the length of the base plate portion 60 in the plate thickness direction, substantially the same as the length of the base plate portion 60 in the plate thickness direction, or longer than the length of the base plate portion 60 in the plate thickness direction.

Further, as shown in FIG. 10, in a case where each of the tube portions 61 extends in the axis direction Y from the other-side surface (specifically, the back surface 601) of the base plate portion 60 in the plate thickness direction and protrudes from the one-side surface (specifically, the front surface 600), the one end 64 is continuous with the outer wall surface 62 (not provided with the reference numeral in FIG. 10) and the rising wall portion 68 in the radial direction. The one end 64 has a one-end surface which extends in the radial direction and the circumferential direction. Although no reference numeral is provided, similarly in FIGS. 11 to 14, the one end 64 is continuous with the outer wall surface 62 and the rising wall portion 68 in the radial direction and has the one-end surface. In addition, the other end 65 is a ridge portion between the side wall proximal end surface and the back surface 601 of the base plate portion 60.

Figure 11:
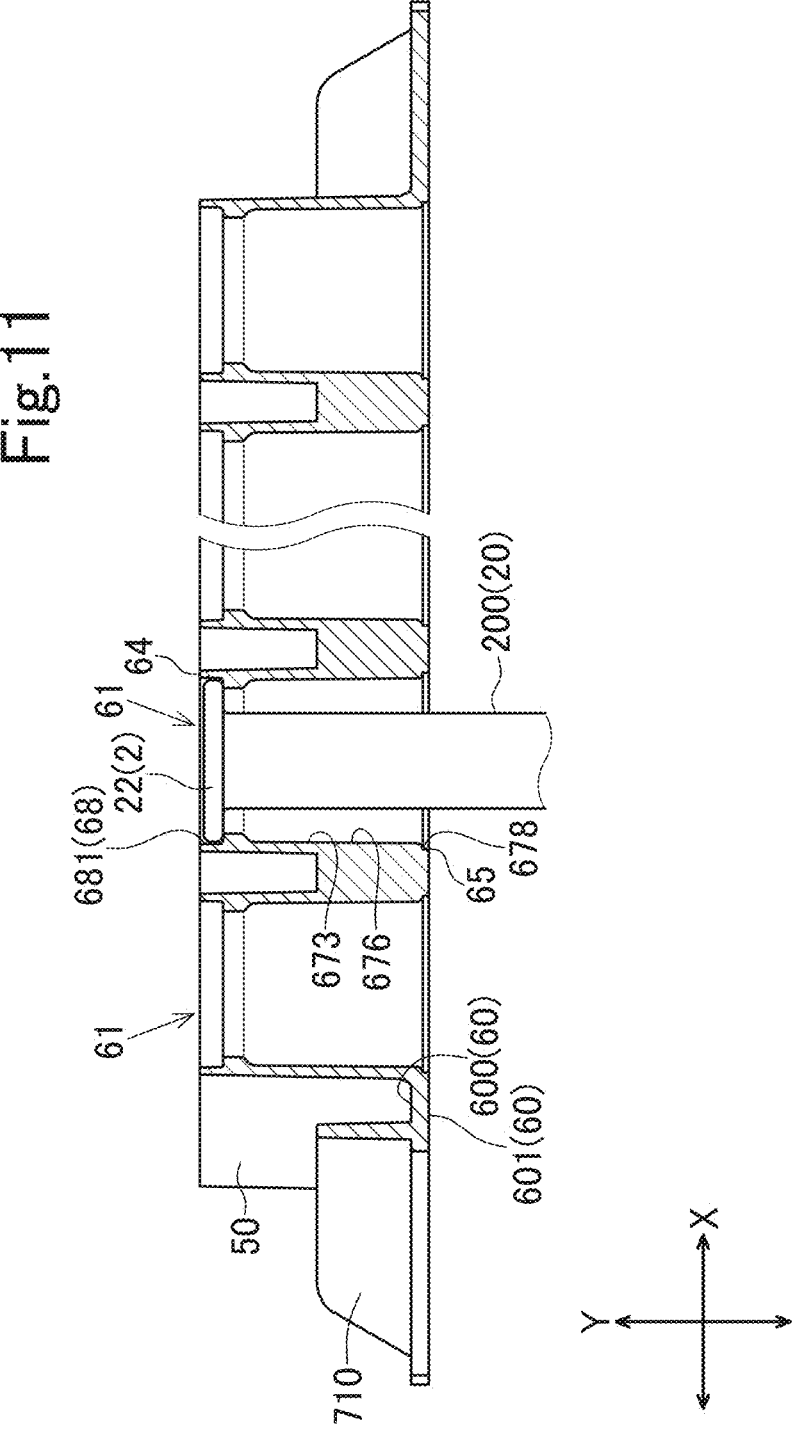
FIG. 11 is a lateral cross-sectional view of the syringe holder in the different form.

As shown in FIGS. 10 and 11, in the whole area in the circumferential direction, a length of the flange abutting portion 681 in the axis direction Y may be longer than the length of the flange portion 22 in the axis direction Y. Accordingly, for example, the flange portion 22 can be inhibited from deviating from the tube portion 61 due to movement of the flange portion 22 supported by the flange support portion 66 to the one side in the axis direction Y. Here, the length of the flange abutting portion 681 in the axis direction Y, which is shown in FIG. 10, is longer than the length of the flange abutting portion 681 in the axis direction Y, which is shown in FIG. 11. On the other hand, a length of the side wall body portion 673 in the axis direction Y, which is shown in FIG. 11, is longer than the length of the side wall body portion 673 in the axis direction Y, which is shown in FIG. 10. Thus, the length of the tube portion 61 in the axis direction Y, which is shown in FIG. 11, is longer than the length of the tube portion 61 in the axis direction Y, which is shown in FIG. 10.

Figure 12:
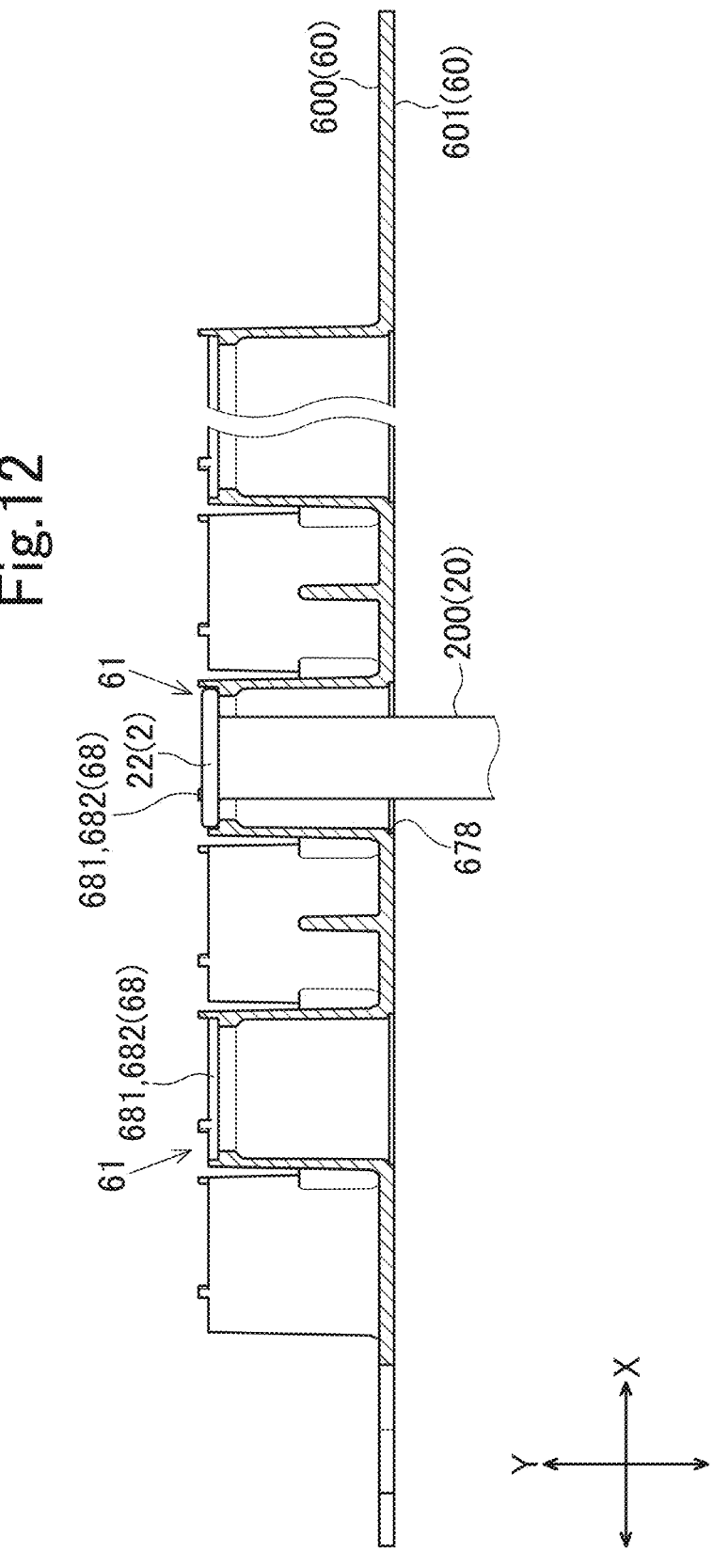
FIG. 12 is a vertical cross-sectional view of the syringe holder in a different form.

Further, as shown in FIG. 12, in a part in the circumferential direction, the length of the flange abutting surface 682 of the flange abutting portion 681 in the axis direction Y may be longer than the length of the flange portion 22 in the axis direction Y. Accordingly, projection portions (not numbered) are formed in the tube portion 61. In FIG. 12, at each predetermined angle (specifically, 120°), the length of the flange abutting surface 682 of the flange abutting portion 681 in the axis direction Y is longer than the length of the flange portion 22 in the axis direction Y.

Figure 13:
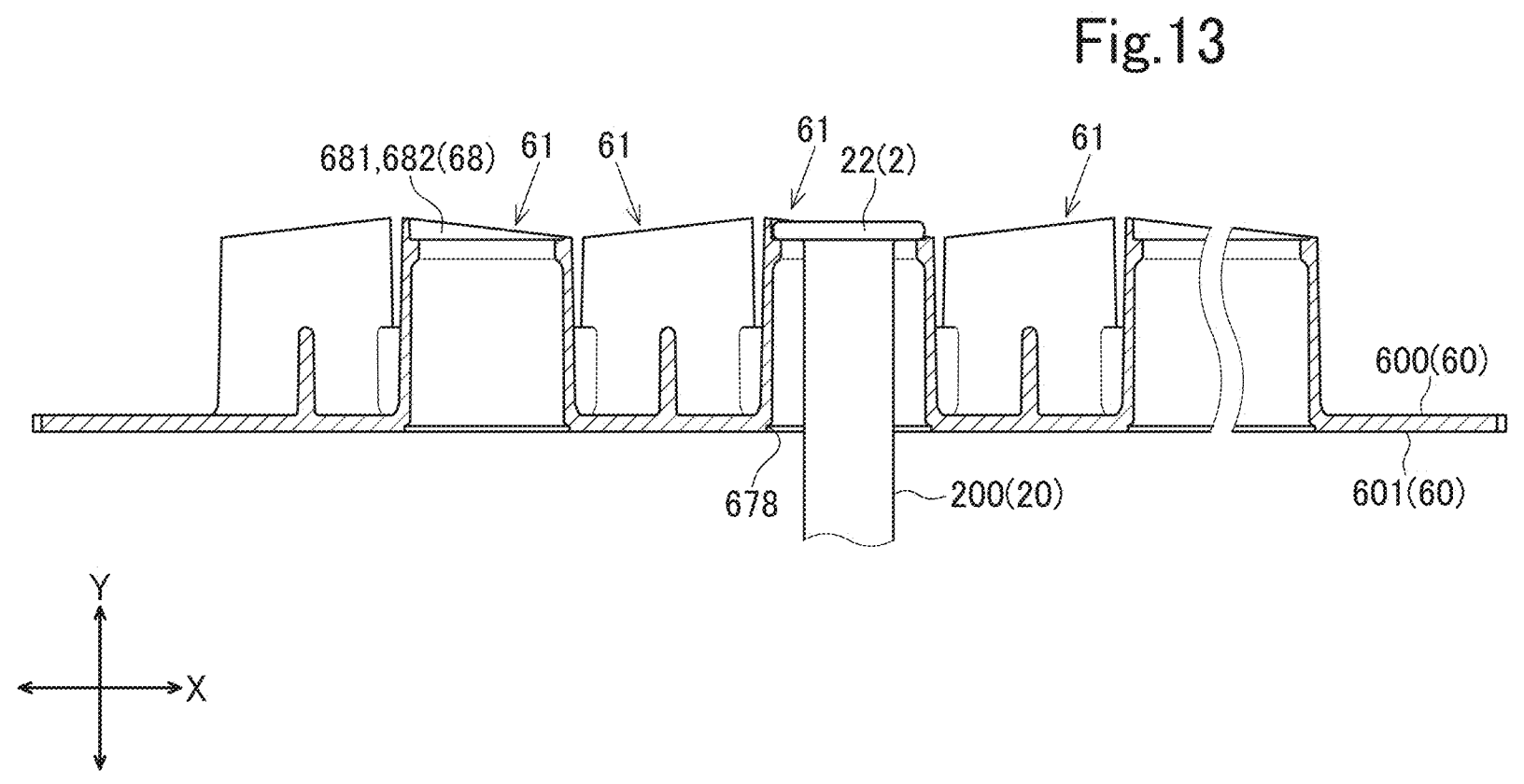
Figure 14:
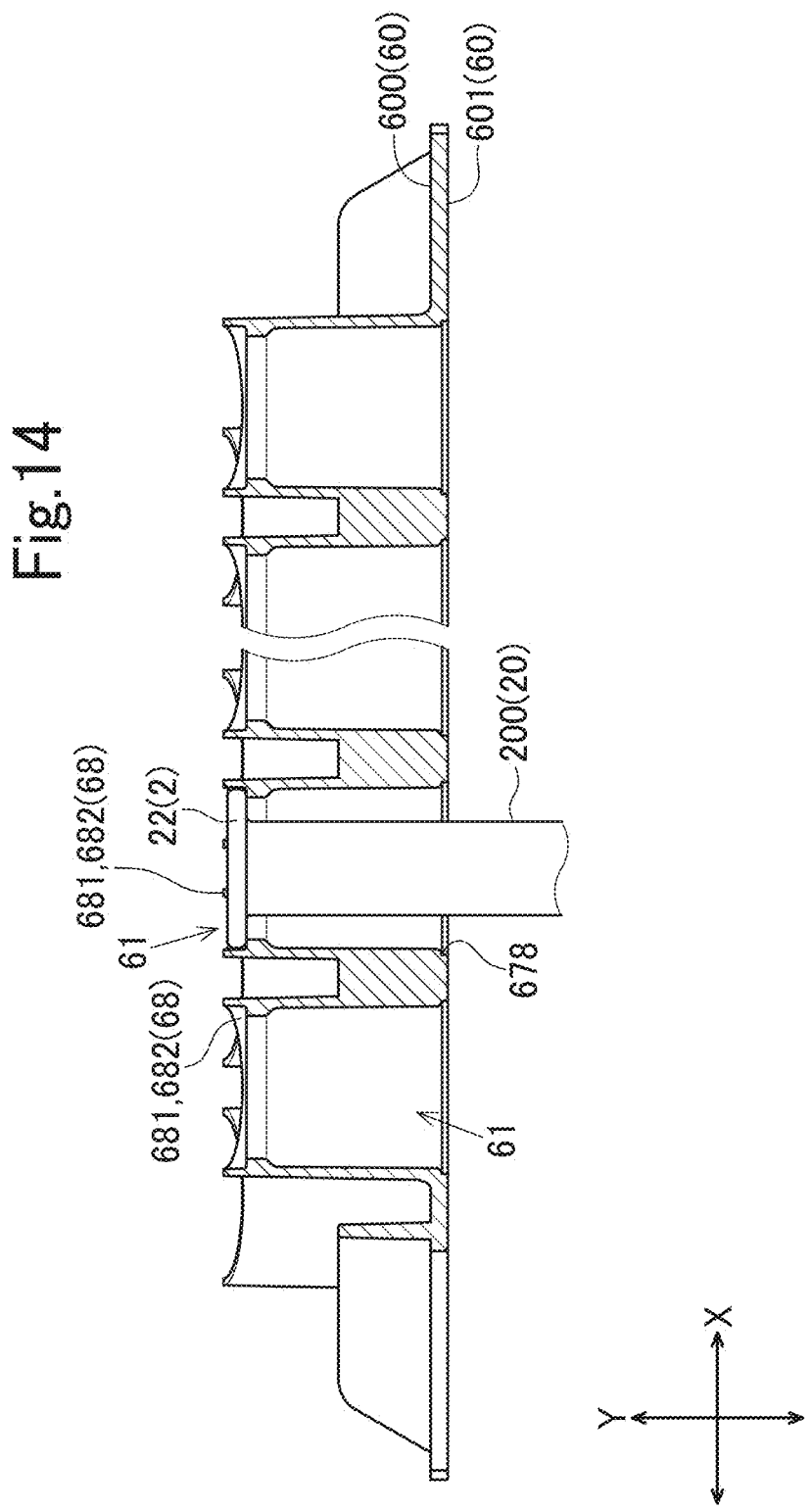
FIG. 14 is a lateral cross-sectional view of the syringe holder in a different form.
Figure 15:
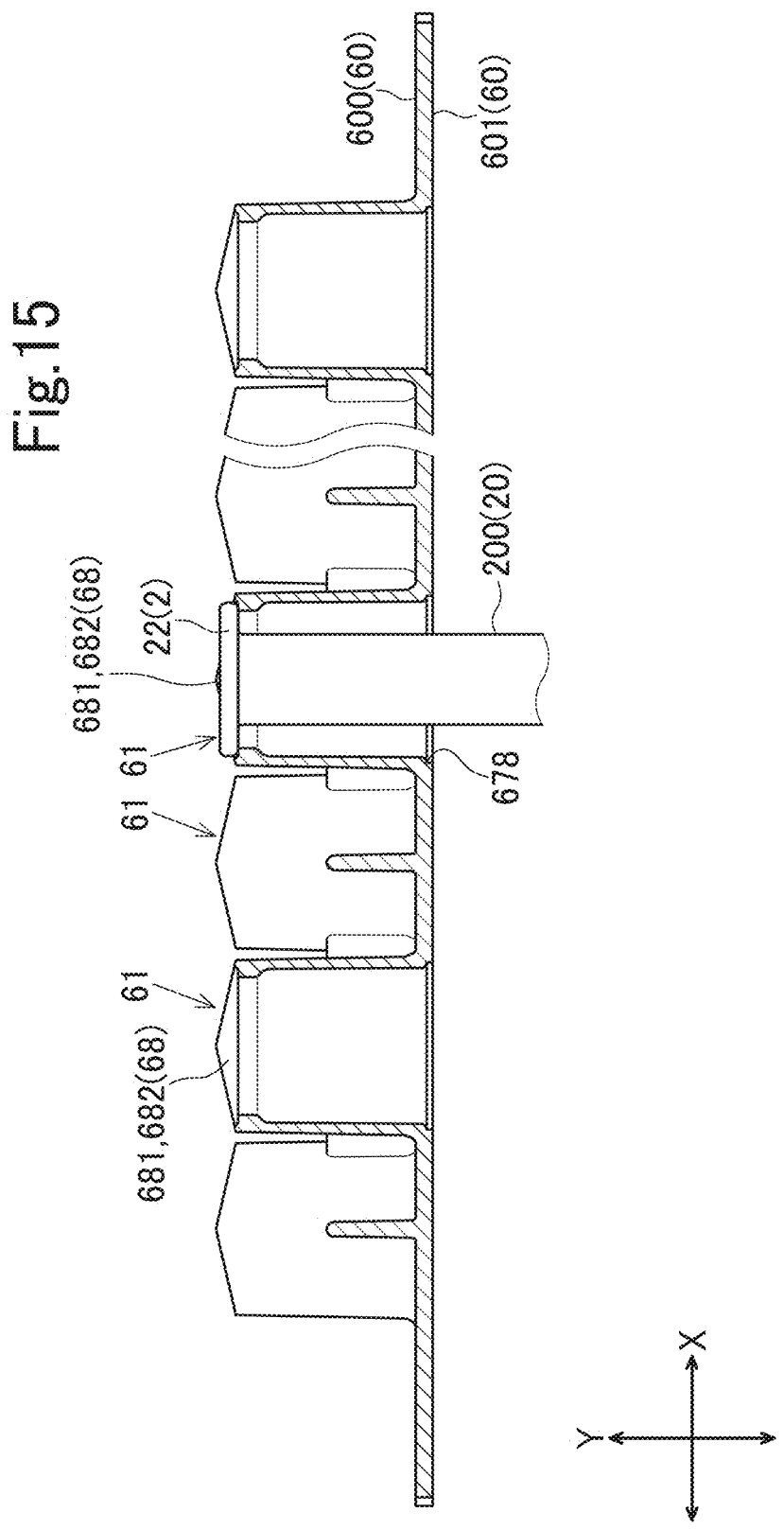
FIG. 15 is a vertical cross-sectional view about the syringe holder in the same form as that in FIG. 14.

Further, as shown in FIGS. 13 to 15, the length of the flange abutting surface 682 of the flange abutting portion 681 in the axis direction Y may be configured to be changed in the circumferential direction. In FIG. 13, in one part in the radial directions (specifically, a left end of a cross section in FIG. 13), the length of the flange abutting surface 682 of the flange abutting portion 681 in the axis direction Y is longest and is longer than the length of the flange portion 22 in the axis direction Y. Further, the length of the flange abutting surface 682 in the axis direction Y gradually becomes shorter from the one part in the radial direction toward another side in the radial directions (specifically, a right side in FIG. 13). Furthermore, the length of the flange abutting surface 682 of the flange abutting portion 681 in the axis direction Y in another part 180° opposed to the one part in the radial directions (specifically, a right end of the cross section in FIG. 13) may be shorter than the length of the flange portion 22 in the axis direction Y.

Meanwhile, as shown in FIG. 14, the length of the flange abutting surface 682 in the axis direction Y may be longest and longer than the length of the flange portion 22 in the axis direction Y in one part and another part in the radial directions. Further, in this case, the length of the flange abutting surface 682 in the axis direction Y may be configured to become shorter toward a radial outside, in a direction orthogonal to a diameter of the one part and the other part in the radial directions. Specifically, as shown in FIG. 15, a configuration is made such that while the one part and the other part in the radial directions (not shown in FIG. 15) are set as vertices, the length of the flange abutting surface 682 in the axis direction Y becomes shorter toward the radial outside in the direction, which is orthogonal to the diameter of the one part and the other part in the radial directions, among the radial directions. In addition, the length of the flange abutting surface 682 in the axis direction Y in a direction which is, at the center of a circular shape, orthogonal to the diameter of the one part and the other part in the radial directions is shortest and shorter than the length of the flange portion 22 in the axis direction Y.

In the above embodiment, a description is made about a case where the base plate portion 60 is configured to have a flat plate shape. However, this is not restrictive, and for example, the base plate portion 60 may be a curved plate. Further, in the above embodiment, a description is made about a case where the base plate portion 60 is a rectangular plate. However, this is not restrictive, and for example, the base plate portion 60 may be a plate which has a circular shape in a plan view.

In the above embodiment, a description is made about a case where the tube portion 61 has a cylindrical shape. However, this is not restrictive, and for example, the tube portion 61 may have a polygonal tubular shape.

In the above embodiment, the cap 21 is configured to be larger than the syringe body 20 in the radial direction. However, this is not restrictive, and for example, the length of the cap 21 in the radial direction may be configured to be a length of the syringe body 20 in the radial direction or shorter. In this case, the tube portion 61 does not have to include the large-diameter guide portion 674.

In the above embodiment, a description is made about a case where the tube portion 61 is shorter than the syringe 2 in the axis direction Y. However, this is not restrictive, and for example, the tube portion 61 may be longer than the syringe 2 in the axis direction Y. In this case, it is possible that when the syringe 2 is inserted into the tube portion 61 and the flange portion 22 (specifically, the flange distal end portion 220) is supported by the flange support portion 66, arrangement of the flange support portion 66 in the tube portion 61 in the axis direction Y is set such that at least the distal end of the syringe 2 is arranged on the other side in the axis direction Y relative to the other end 65 of the tube portion 61.

In the above embodiment, a description is made about a case where the plurality of tube portions 61 are arranged in the base plate portion 60. However, this is not restrictive, and for example, one tube portion 61 may be arranged in the base plate portion 60. In this case, the syringe holder 5 is capable of holding one syringe 2.

In the above embodiment, a description is made about a case where all of the tube portions 61 arranged in the base plate portion 60 have the same configuration. However, this is not restrictive, and for example, the plurality of tube portions 61 arranged in the base plate portion 60 may be configured to be different from each other.

In the above embodiment, a description is made about a case where the length of the outer wall surface 62 in the axis direction Y is longer than the length of the base plate portion 60 in the plate thickness direction. However, this is not restrictive, and for example, the length of the outer wall surface 62 in the axis direction Y may be shorter than the length of the base plate portion 60 in the plate thickness direction.

In the above embodiment, the support surface 660 is configured to extend in the radial direction. However, this is not restrictive, and for example, the support surface 660 may be configured as an inclined surface (for example, a curved surface or a flat surface) which extends to the one side or the other side in the axis direction Y toward the radially inner side. Further, the support surface 660 may be an uneven surface.

In the above embodiment, the support surface 660 is configured to extend in the whole circumference in the circumferential direction. Thus, the flange support portion 66 is arranged throughout the whole circumference in the circumferential direction. However, for example, a plurality of flange support portions 66 may be arranged at predetermined intervals in the circumferential direction.

In the above embodiment, the syringe abutting surface 672 of the syringe abutting portion 671 is formed in the whole circumference in the circumferential direction. Thus, the syringe abutting portion 671 is arranged throughout the whole area in the circumferential direction. However, this is not restrictive, and for example, a plurality of syringe abutting portions 671 may be arranged at predetermined intervals in the circumferential direction.

In the above embodiment, a description is made about a case where the syringe abutting surface 672 of the syringe abutting portion 671 is continuous with the support surface 660 and the syringe abutting portion 671 is thereby continuous with the flange support portion 66. However, this is not restrictive, and for example, the syringe abutting portion 671 and the flange support portion 66 may be arranged to be separated in the axis direction Y.

In the above embodiment, a description is made about a case where the side wall portion 67 includes the syringe abutting portion 671 and the side wall body portion 673 which is arranged on the radially outer side relative to the syringe abutting portion 671. However, this is not restrictive, and for example, the side wall portion 67 does not have to include the side wall body portion 673. In this case, the syringe abutting portion 671 is continuous with the other end 65.

In the above embodiment, the large-diameter guide surface 675 is continuous with the syringe abutting surface 672 of the syringe abutting portion 671, and the large-diameter guide portion 674 is thereby continuous with the syringe abutting portion 671 in the axis direction Y. However, this is not restrictive, and for example, the large-diameter guide portion 674 and the syringe abutting portion 671 may be arranged to be separated in the axis direction Y.

In the above embodiment, the large-diameter guide surface 675 is the inclined surface in which the inner diameter of the tube portion 61 becomes smaller toward the one side in the axis direction Y. The "inclined surface" mentioned herein includes a curved surface which is curved to the radially inner side as it advances from the other side toward the one side in the axis direction Y and a flat surface. Thus, the large-diameter guide surface 675 may be configured as a curved surface in which a separation distance between the inner periphery surface and the outer periphery surface of the tube portion 61 in the radial direction becomes longer toward the one side in the axis direction Y. Alternatively, the large-diameter guide surface 675 may be configured as a curved surface in which the separation distance between the inner periphery surface and the outer periphery surface of the tube portion 61 in the radial direction becomes shorter toward the one side in the axis direction Y.

In the above embodiment, a description is made about a case where the rising wall portion 68 is shorter than the side wall portion 67 in the axis direction Y. However, this is not restrictive, and the rising wall portion 68 may be longer than the side wall portion 67 in the axis direction Y.

In the above embodiment, the flange abutting surface 682 of the flange abutting portion 681 is configured to extend in the axis direction Y. However, this is not restrictive, and for example, the flange abutting surface 682 of the flange abutting portion 681 may be an inclined surface (specifically, a flat surface or a curved surface) in which the inner diameter of the tube portion 61 becomes smaller or larger toward the other side in the axis direction Y.

In the above embodiment, the flange abutting surface 682 is continuous from the end of the support surface 660 on the radially outer side, the support surface 660 extending in the radial direction, to the one side in the axis direction Y. Accordingly, the flange support portion 66 is continuous with the flange abutting portion 681 in the axis direction Y. However, this is not restrictive, and the flange support portion 66 and the flange abutting portion 681 may be arranged to be separated in the axis direction Y.

In the above embodiment, the flange guide surface 684 is continuous with the flange abutting surface 682. Thus, the flange guide portion 683 in the above embodiment is continuous with the flange abutting portion 681. However, this is not restrictive, and for example, the flange guide portion 683 may be arranged to be separated from the flange abutting portion 681 on the one side in the axis direction Y relative to the flange abutting portion 681.

In the above embodiment, because the flange guide surface 684 extends in the whole area in the circumferential direction, the flange guide portion 683 is formed throughout the whole area in the circumferential direction. However, this is not restrictive, and for example, a plurality of flange guide portions 683 may be arranged at predetermined intervals in the circumferential direction.

In the above embodiment, the flange guide surface 684 is configured as the inclined surface in which the inner diameter of the tube portion 61 becomes smaller toward the other side in the axis direction Y. The "inclined surface" mentioned herein includes a curved surface which is curved to the radially inner side as it advances from the one side toward the other side in the axis direction Y and a flat surface. Thus, the flange guide surface 684 may be configured as a curved surface in which the separation distance between the inner periphery surface and the outer periphery surface of the tube portion 61 in the radial direction becomes longer toward the other side in the axis direction Y. Alternatively, the flange guide surface 684 may be configured as a curved surface in which the separation distance between the inner periphery surface and the outer periphery surface of the tube portion 61 in the radial direction becomes shorter toward the other side in the axis direction Y.

In the above embodiment, a description is made about a case where the syringes 2 are held by the syringe holder 5 and the syringe holder 5 is thereafter housed in the container body 8. However, this is not restrictive, and the syringes 2 may be held by the syringe holder 5 after the syringe holder 5 is housed in the container body 8.

In the above embodiment, a description is made about a case where the assembled package 1 is transported in the inverted posture. However, this is not restrictive, and the package 1 may be transported in the upright posture. Further, in the above embodiment, a description is made about a case where at the transportation destination, the distal end sides of the syringes 2 are inserted through the insertion holes of the punching plates. However, this is not restrictive, and it is possible that while the distal end sides of the syringes 2 held by the syringe holder 5 are not inserted through the insertion holes of the punching plates, the syringe holder 5 is set in the filling device.

In the above embodiment, a description is made about a case where the trunk portion 200 has the drug solution filling portion as the portion to be filled with a drug solution. However, for example, on the outer periphery surface of the drug solution filling portion in the trunk portion 200, a scale (not shown) for checking a filled solution amount may be provided by printing. In this case, the abutting portion 201 is an area between the scale provided on the outer periphery surface of the trunk portion 200 and the flange portion 22. Furthermore, even when the abutting portion 201 abuts the syringe abutting portion 671 and the outer periphery surface of the trunk portion 200 is scratched, the outer periphery surface on the distal end side relative to the abutting portion 201 (specifically, the drug solution filling portion) in the outer periphery surface of the trunk portion 200 is prevented from being scratched, and a situation can thereby be prevented where the printed scale is peeled off and cannot be read. In addition, in this case, the large-diameter portion is arranged on the other side in the axis direction Y relative to the scale.

In the above embodiment, a description is made about a case where the outer diameter of the periphery tube portion 203 is smaller than the outer diameter of the trunk portion 200. However, this is not restrictive, and the outer diameter of the periphery tube portion 203 may be configured to be larger than the outer diameter of the trunk portion 200. In this case, in addition to or instead of the cap 21, the periphery tube portion 203 may be configured as the large-diameter portion.

In the above embodiment, a description is made about a case where the large-diameter portion configured with the cap 21 is arranged at the distal end of the trunk portion 200. However, this is not restrictive, and for example, the large-diameter portion is not configured with the cap 21 but protrudes from the outer periphery surface in the distal end portion of the trunk portion 200 and may thereby be configured to have a diameter larger than the trunk portion 200. In this case, the syringe 2 does not have to include the periphery tube portion 203. Alternatively, the syringe 2 may include only the needle protection portion. In this case, it is possible that the needle protection portion is configured as the large-diameter portion. In addition, the large-diameter portion may be not only a portion, which covers the injection needle 204, such as the cap 21 or the needle protection portion but also a mounting member, which is configured to have a diameter larger than the trunk portion 200 and is mounted on the distal end portion of the syringe body 20, for example.

REFERENCE SIGNS LIST

1: Package
2: Syringe
20: Syringe body
200: Trunk portion

201: Abutting portion
202: Holding portion
203: Periphery tube portion
204: Injection needle
21: Cap
22: Flange portion
220: Flange distal end portion
221: Flange edge portion
3: Syringe housing container
4: Protection film
5: Syringe holder
50: Cutout
6: Holding body
60: Base plate portion
600: Front surface
601: Back surface
61: Tube portion
62: Outer wall surface
63: Inner wall surface
64: One end
65: Other end
66: Flange support portion
660: Support surface
67: Side wall portion
671: Syringe abutting portion
672: Syringe abutting surface
673: Side wall body portion
674: Large-diameter guide portion
675: Large-diameter guide surface
676: Side wall other-side portion
677: Side wall other-side surface
68: Rising wall portion
681: Flange abutting portion
682: Flange abutting surface
683: Flange guide portion
684: Flange guide surface
7: Periphery portion
70: Step portion
700: Vertical step portion
701: Lateral step portion
71: Placing portion
710: Extension portion
8: Container body
80: Bottom portion
81: Side wall portion
810: Width side wall portion
811: Longitudinal side wall portion
812: Lower-section side wall portion
813: Upper-section side wall portion
814: Side wall step portion
815: Brim portion

The invention claimed is:

1. A syringe holder comprising:
a base plate portion having a plate shape; and a tube portion being formed in a tubular shape having an axis direction being provided along a plate thickness direction of the base plate portion, the tube portion being configured to allow a syringe to be inserted through the tube portion from one side to another side in the axis direction, the syringe including a syringe body which has a tubular shape and a flange portion which protrudes from an outer periphery surface of the syringe body to an outer side in a radial direction,
the syringe body including a trunk portion which has a tubular shape and is configured to store a solution,
the syringe includes a large-diameter portion arranged in a distal end portion of the trunk portion and configured to be larger than the trunk portion in the radial direction,
wherein the tube portion includes a flange support portion which supports the flange portion of the inserted syringe from the other side in the axis direction and a flange abutting portion which is arranged on the one side in the axis direction and on an outer side in the radial direction, relative to the flange support portion, the flange abutting portion being configured to be capable of abutting, in the radial direction, the flange portion supported by the flange support portion, and a side wall portion arranged on the other side in the axis direction relative to the flange support portion,
the side wall portion includes a syringe abutting portion, and a side wall body portion which is arranged on the other side in the axis direction relative to the syringe abutting portion and on a radially outer side relative to the syringe abutting portion,
the syringe abutting portion being arranged on the other side in the axis direction and on an inner side in the radial direction, relative to the flange support portion, and is configured to be capable of abutting a portion of the syringe body, the portion being in vicinity to the flange portion in the syringe body on the other side in the axis direction relative to the flange portion,
the side wall body portion includes a large-diameter guide portion which guides the large-diameter portion to an inner side in the radial direction, and a side wall other-side portion which is arranged on the other side in the axis direction and on the outer side in the radial direction, relative to the large-diameter guide portion,
wherein the large-diameter guide portion is arranged on the other side in the axis direction relative to the syringe abutting portion and is configured to have a diameter decreasing from the other side toward the one side in the axis direction, and
the syringe abutting portion is continuous with the large-diameter portion in the axis direction.

2. The syringe holder according to claim 1, wherein
the tube portion includes a flange guide portion which guides the flange portion to an inner side in the radial direction, and
the flange guide portion is arranged on the one side in the axis direction and on an outer side in the radial direction, relative to the flange abutting portion, and is configured to have a diameter decreasing from the one side toward the other side in the axis direction.

3. A package comprising:
the syringe holder according to claim 1;
the syringe; and
a container body for housing the syringe holder.

* * * * *